(12) United States Patent
O'Mahony

(10) Patent No.: US 7,491,796 B1
(45) Date of Patent: Feb. 17, 2009

(54) RETRO-INVERSION PEPTIDES THAT TARGET GIT RECEPTORS AND RELATED METHODS

(75) Inventor: Daniel Joseph O'Mahony, Dublin (IE)

(73) Assignee: Merrion Research III Limited, Dublin (IE)

( * ) Notice: Subject to any disclaimer, the term of this patent is extended or adjusted under 35 U.S.C. 154(b) by 0 days.

(21) Appl. No.: 09/443,986

(22) Filed: Nov. 19, 1999

Related U.S. Application Data

(60) Provisional application No. 60/109,038, filed on Nov. 19, 1998.

(51) Int. Cl.
*C07K 1/00* (2006.01)
(52) U.S. Cl. .......................... 530/350; 530/300; 514/2; 514/12
(58) Field of Classification Search .............. 530/300, 530/350; 435/7.1; 514/2, 21
See application file for complete search history.

(56) References Cited

U.S. PATENT DOCUMENTS 6,703,362 B1 * 3/2004 Alvarez et al. ................ 514/12

FOREIGN PATENT DOCUMENTS

WO        WO98/51325       * 11/1998

* cited by examiner

*Primary Examiner*—Hope A Robinson
(74) *Attorney, Agent, or Firm*—Meyers Bigel Sibley & Sajovec, P.A.

(57) ABSTRACT

Retro-inverted forms of GIT targeting agents that target specific receptor sites in vivo and/or promote uptake of active agents and/or enhance active agent delivery across the GIT into the systemic circulation are provided. These retro-inverted peptides and compositions containing these retro-inverted peptides can be used to deliver an active agent, such as a drug or a drug-containing nano- or microparticle for treatment of a condition in a subject in need of the drug, in vivo. Additionally, the invention provides antibodies which are capable of immunospecifically binding the retro-inverted peptides.

7 Claims, 2 Drawing Sheets

SEQUENCE LISTING

```
<160> NUMBER OF SEQ ID NOS: 85

<210> SEQ ID NO 1
<211> LENGTH: 15
<212> TYPE: PRT
<213> ORGANISM: Artificial Sequence
<220> FEATURE:
<223> OTHER INFORMATION: PAX2 15 mer fragment-D form retroinversion

<400> SEQUENCE: 1

Arg Thr Arg Leu Arg Arg Asn His Ser Ser His Lys Ala Asn Thr
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: P31 16 mer fragment-D form retroinversion

<400> SEQUENCE: 2

Gly Pro His Arg Arg Gly Arg Pro Asn Ser Arg Ser Ser Lys Arg Thr
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: HAX42 14 mer fragment-D form retroinversion

<400> SEQUENCE: 3

Gly Thr Ser Asn Gly Asn Gly Cys Cys Asn Tyr Asp Gly Pro
1               5                   10

<210> SEQ ID NO 4
<211> LENGTH: 15
<212> TYPE: PRT
<213> ORGANISM: Artificial Sequence
<220> FEATURE:
<223> OTHER INFORMATION: PAX2 15 mer fragment

<400> SEQUENCE: 4
```

```
Thr Asn Ala Lys His Ser Ser His Asn Arg Arg Leu Arg Thr Arg
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: P31 16 mer fragment

<400> SEQUENCE: 5

Thr Arg Lys Ser Ser Arg Ser Asn Pro Arg Gly Arg Arg His Pro Gly
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: HAX42 14 mer fragment

<400> SEQUENCE: 6

Pro Gly Asp Tyr Asn Cys Cys Gly Asn Gly Asn Ser Thr Gly
1               5                   10

<210> SEQ ID NO 7
<211> LENGTH: 40
<212> TYPE: PRT
<213> ORGANISM: Artificial Sequence
<220> FEATURE:
<223> OTHER INFORMATION: PAX2 full length

<400> SEQUENCE: 7

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn Arg Arg Leu
                20                  25                  30

Arg Thr Arg Ser Arg Pro Asn Gly
                35                  40

<210> SEQ ID NO 8
<211> LENGTH: 45
<212> TYPE: PRT
<213> ORGANISM: Artificial Sequence
<220> FEATURE:
<223> OTHER INFORMATION: HAX42 full length, N-terminal Lysine is
      dansylated
<220> FEATURE:
<221> NAME/KEY: MOD_RES
<222> LOCATION: (1)..(1)
<223> OTHER INFORMATION: Dansylated L-Lysine

<400> SEQUENCE: 8

Lys Ser Asp His Ala Leu Gly Thr Asn Leu Arg Ser Asp Asn Ala Lys
1               5                   10                  15

Glu Pro Gly Asp Tyr Asn Cys Cys Gly Asn Gly Asn Ser Thr Gly Arg
                20                  25                  30

Lys Val Phe Asn Arg Arg Arg Pro Ser Ala Ile Pro Thr
                35                  40                  45

<210> SEQ ID NO 9
<211> LENGTH: 16
<212> TYPE: PRT
<213> ORGANISM: Artificial Sequence
<220> FEATURE:
<223> OTHER INFORMATION: ZElan 144; PAX2 15 mer fragment-D form
```

-continued

```
      retroinversion with additional L-lysine in position 1
<220> FEATURE:
<221> NAME/KEY: MOD_RES
<222> LOCATION: (1)..(1)
<223> OTHER INFORMATION: Dansylated L-lysine

<400> SEQUENCE: 9

Lys Arg Thr Arg Leu Arg Arg Asn His Ser Ser His Lys Ala Asn Thr
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: ZElan 145; P31 16 mer fragment-D form
      retroinversion with additional L-lysine in position 1
<220> FEATURE:
<221> NAME/KEY: MOD_RES
<222> LOCATION: (1)..(1)
<223> OTHER INFORMATION: dansylated L-lysine

<400> SEQUENCE: 10

Lys Gly Pro His Arg Arg Gly Arg Pro Asn Ser Arg Ser Ser Lys Arg
1               5                   10                  15

Thr

<210> SEQ ID NO 11
<211> LENGTH: 15
<212> TYPE: PRT
<213> ORGANISM: Artificial Sequence
<220> FEATURE:
<223> OTHER INFORMATION: ZElan 146; HAX42 14 mer fragment-D form
      retroinversion with additional L-Lysine in position 1
<220> FEATURE:
<221> NAME/KEY: MOD_RES
<222> LOCATION: (1)..(1)
<223> OTHER INFORMATION: dansylated L-Lysine

<400> SEQUENCE: 11

Lys Gly Thr Ser Asn Gly Asn Gly Cys Cys Asn Tyr Asp Gly Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: ZElan 129; PAX2 15 mer fragment with additional
      L-Lysine in position 1
<220> FEATURE:
<221> NAME/KEY: MOD_RES
<222> LOCATION: (1)..(1)
<223> OTHER INFORMATION: dansylated L-Lysine

<400> SEQUENCE: 12

Lys Thr Asn Ala Lys His Ser Ser His Asn Arg Arg Leu Arg Thr Arg
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: ZElan 031; P31 16 mer fragment with additional
      L-Lysine in position 1
<220> FEATURE:
<221> NAME/KEY: MOD_RES
<222> LOCATION: (1)..(1)
<223> OTHER INFORMATION: dansylated L-Lysine
```

```
<400> SEQUENCE: 13

Lys Thr Arg Lys Ser Ser Arg Ser Asn Pro Arg Gly Arg His Pro
1               5                   10                  15

Gly

<210> SEQ ID NO 14
<211> LENGTH: 15
<212> TYPE: PRT
<213> ORGANISM: Artificial Sequence
<220> FEATURE:
<223> OTHER INFORMATION: ZElan 091; HAX42 14 mer fragment with
      additional L-lysine in position 1
<220> FEATURE:
<221> NAME/KEY: MOD_RES
<222> LOCATION: (1)..(1)
<223> OTHER INFORMATION: dansylated L-lysine

<400> SEQUENCE: 14

Lys Pro Gly Asp Tyr Asn Cys Cys Gly Asn Gly Asn Ser Thr Gly
1               5                   10                  15

<210> SEQ ID NO 15
<211> LENGTH: 41
<212> TYPE: PRT
<213> ORGANISM: Artificial Sequence
<220> FEATURE:
<223> OTHER INFORMATION: PAX2 full length, N-terminal Lysine is
      dansylated
<220> FEATURE:
<221> NAME/KEY: MOD_RES
<222> LOCATION: (1)..(1)
<223> OTHER INFORMATION: dansylated L-Lysine

<400> SEQUENCE: 15

Lys Ser Thr Pro Pro Ser Arg Glu Ala Tyr Ser Arg Pro Tyr Ser Val
1               5                   10                  15

Asp Ser Asp Ser Asp Thr Asn Ala Lys His Ser Ser His Asn Arg Arg
                20                  25                  30

Leu Arg Thr Arg Ser Arg Pro Asn Gly
        35                  40

<210> SEQ ID NO 16
<211> LENGTH: 44
<212> TYPE: PRT
<213> ORGANISM: Artificial Sequence
<220> FEATURE:
<223> OTHER INFORMATION: S15 44 mer fragment L-form

<400> SEQUENCE: 16

Arg Ser Gly Ala Tyr Glu Ser Pro Asp Gly Arg Gly Arg Ser Tyr
1               5                   10                  15

Val Gly Gly Gly Gly Gly Cys Gly Asn Ile Gly Arg Lys His Asn Leu
                20                  25                  30

Trp Gly Leu Arg Thr Ala Ser Pro Ala Cys Trp Asp
        35                  40

<210> SEQ ID NO 17
<211> LENGTH: 44
<212> TYPE: PRT
<213> ORGANISM: Artificial Sequence
<220> FEATURE:
<223> OTHER INFORMATION: S21 44 mer fragment L-form

<400> SEQUENCE: 17
```

```
Ser Pro Arg Ser Phe Trp Pro Val Val Ser Arg His Glu Ser Phe Gly
1               5                   10                  15

Ile Ser Asn Tyr Leu Gly Cys Gly Tyr Arg Thr Cys Ile Ser Gly Thr
            20                  25                  30

Met Thr Lys Ser Ser Pro Ile Tyr Pro Arg His Ser
        35                  40
```

<210> SEQ ID NO 18
<211> LENGTH: 44
<212> TYPE: PRT
<213> ORGANISM: Artificial Sequence
<220> FEATURE:
<223> OTHER INFORMATION: S22 44 mer fragment L-form

<400> SEQUENCE: 18

```
Ser Ser Ser Ser Asp Trp Gly Gly Val Pro Gly Lys Val Val Arg Glu
1               5                   10                  15

Arg Phe Lys Gly Arg Gly Cys Gly Ile Ser Ile Thr Ser Val Leu Thr
            20                  25                  30

Gly Lys Pro Asn Pro Cys Pro Glu Pro Lys Ala Ala
        35                  40
```

<210> SEQ ID NO 19
<211> LENGTH: 44
<212> TYPE: PRT
<213> ORGANISM: Artificial Sequence
<220> FEATURE:
<223> OTHER INFORMATION: Sni10 44 mer fragment L-form

<400> SEQUENCE: 19

```
Arg Val Gly Gln Cys Thr Asp Ser Asp Val Arg Arg Pro Trp Ala Arg
1               5                   10                  15

Ser Cys Ala His Gln Gly Cys Gly Ala Gly Thr Arg Asn Ser His Gly
            20                  25                  30

Cys Ile Thr Arg Pro Leu Arg Gln Ala Ser Ala His
        35                  40
```

<210> SEQ ID NO 20
<211> LENGTH: 39
<212> TYPE: PRT
<213> ORGANISM: Artificial Sequence
<220> FEATURE:
<223> OTHER INFORMATION: Sni28 39 mer fragment L-form

<400> SEQUENCE: 20

```
Ser His Ser Gly Gly Met Asn Arg Ala Tyr Gly Asp Val Phe Arg Glu
1               5                   10                  15

Leu Arg Asp Arg Trp Asn Ala Thr Ser His His Thr Arg Pro Thr Pro
            20                  25                  30

Gln Leu Pro Arg Gly Pro Asn
        35
```

<210> SEQ ID NO 21
<211> LENGTH: 41
<212> TYPE: PRT
<213> ORGANISM: Artificial Sequence
<220> FEATURE:
<223> OTHER INFORMATION: Sni34 41 mer fragment L-form

<400> SEQUENCE: 21

```
Ser Pro Cys Gly Gly Ser Trp Gly Arg Phe Met Gln Gly Gly Leu Phe
1               5                   10                  15
```

-continued

Gly Gly Arg Thr Asp Gly Cys Gly Ala His Arg Asn Arg Thr Ser Ala
            20                  25                  30

Ser Leu Glu Pro Pro Ser Ser Asp Tyr
            35                  40

<210> SEQ ID NO 22
<211> LENGTH: 39
<212> TYPE: PRT
<213> ORGANISM: Artificial Sequence
<220> FEATURE:
<223> OTHER INFORMATION: Sni38 39 mer fragment L-form

<400> SEQUENCE: 22

Arg Gly Ala Ala Asp Gln Arg Arg Gly Trp Ser Glu Asn Leu Gly Leu
1               5                   10                  15

Pro Arg Val Gly Trp Asp Ala Ile Ala His Asn Ser Tyr Thr Phe Thr
            20                  25                  30

Ser Arg Arg Pro Arg Pro Pro
            35

<210> SEQ ID NO 23
<211> LENGTH: 44
<212> TYPE: PRT
<213> ORGANISM: Artificial Sequence
<220> FEATURE:
<223> OTHER INFORMATION: Sni45 44 mer fragment L-form

<400> SEQUENCE: 23

Ser Gly Gly Glu Val Ser Ser Trp Gly Arg Val Asn Asp Leu Cys Ala
1               5                   10                  15

Arg Val Ser Trp Thr Gly Cys Gly Thr Ala Arg Ser Ala Arg Thr Asp
            20                  25                  30

Asn Lys Gly Phe Leu Pro Lys His Ser Ser Leu Arg
            35                  40

<210> SEQ ID NO 24
<211> LENGTH: 44
<212> TYPE: PRT
<213> ORGANISM: Artificial Sequence
<220> FEATURE:
<223> OTHER INFORMATION: SniAX2 44 mer fragment L-form

<400> SEQUENCE: 24

Ser Asp Ser Asp Gly Asp His Tyr Gly Leu Arg Gly Gly Val Arg Cys
1               5                   10                  15

Ser Leu Arg Asp Arg Gly Cys Gly Leu Ala Leu Ser Thr Val His Ala
            20                  25                  30

Gly Pro Pro Ser Phe Tyr Pro Lys Leu Ser Ser Pro
            35                  40

<210> SEQ ID NO 25
<211> LENGTH: 39
<212> TYPE: PRT
<213> ORGANISM: Artificial Sequence
<220> FEATURE:
<223> OTHER INFORMATION: SniAX4 39 mer fragment L-form

<400> SEQUENCE: 25

Arg Ser Leu Gly Asn Tyr Gly Val Thr Gly Thr Val Asp Val Thr Val
1               5                   10                  15

Leu Pro Met Pro Gly His Ala Asn His Leu Gly Val Ser Ser Ala Ser
            20                  25                  30

```
Ser Ser Asp Pro Arg Arg
        35

<210> SEQ ID NO 26
<211> LENGTH: 38
<212> TYPE: PRT
<213> ORGANISM: Artificial Sequence
<220> FEATURE:
<223> OTHER INFORMATION: SniAX6 38 mer fragment L-form

<400> SEQUENCE: 26

Arg Thr Thr Thr Ala Lys Gly Cys Leu Leu Gly Ser Phe Gly Val Leu
1               5                   10                  15

Ser Gly Cys Ser Phe Thr Pro Thr Ser Pro Pro His Leu Gly Tyr
            20                  25                  30

Pro Pro His Ser Val Asn
        35

<210> SEQ ID NO 27
<211> LENGTH: 39
<212> TYPE: PRT
<213> ORGANISM: Artificial Sequence
<220> FEATURE:
<223> OTHER INFORMATION: SniAX8 39 mer fragment L-form

<400> SEQUENCE: 27

Ser Pro Lys Leu Ser Ser Val Gly Val Met Thr Lys Val Thr Glu Leu
1               5                   10                  15

Pro Thr Glu Gly Pro Asn Ala Ile Ser Ile Pro Ile Ser Ala Thr Leu
            20                  25                  30

Gly Pro Arg Asn Pro Leu Arg
        35

<210> SEQ ID NO 28
<211> LENGTH: 39
<212> TYPE: PRT
<213> ORGANISM: Artificial Sequence
<220> FEATURE:
<223> OTHER INFORMATION: DAB3 39 mer fragment L-form

<400> SEQUENCE: 28

Arg Trp Cys Gly Ala Glu Leu Cys Asn Ser Val Thr Lys Lys Phe Arg
1               5                   10                  15

Pro Gly Trp Arg Asp His Ala Asn Pro Ser Thr His His Arg Thr Pro
            20                  25                  30

Pro Pro Ser Gln Ser Ser Pro
        35

<210> SEQ ID NO 29
<211> LENGTH: 44
<212> TYPE: PRT
<213> ORGANISM: Artificial Sequence
<220> FEATURE:
<223> OTHER INFORMATION: DAB7 44 mer fragment L-form

<400> SEQUENCE: 29

Arg Trp Cys Gly Ala Asp Asp Pro Cys Gly Ala Ser Arg Trp Arg Gly
1               5                   10                  15

Gly Asn Ser Leu Phe Gly Cys Gly Leu Arg Cys Ser Ala Ala Gln Ser
            20                  25                  30

Thr Pro Ser Gly Arg Ile His Ser Thr Ser Thr Ser
        35                  40
```

```
<210> SEQ ID NO 30
<211> LENGTH: 39
<212> TYPE: PRT
<213> ORGANISM: Artificial Sequence
<220> FEATURE:
<223> OTHER INFORMATION: DAB10 39 mer fragment L-form

<400> SEQUENCE: 30

Ser Lys Ser Gly Glu Gly Gly Asp Ser Ser Arg Gly Glu Thr Gly Trp
1               5                   10                  15

Ala Arg Val Arg Ser His Ala Met Thr Ala Gly Arg Phe Arg Trp Tyr
            20                  25                  30

Asn Gln Leu Pro Ser Asp Arg
        35

<210> SEQ ID NO 31
<211> LENGTH: 38
<212> TYPE: PRT
<213> ORGANISM: Artificial Sequence
<220> FEATURE:
<223> OTHER INFORMATION: DAB18 38 mer fragment L-form

<400> SEQUENCE: 31

Arg Ser Ser Ala Asn Asn Cys Glu Trp Lys Ser Asp Trp Met Arg Arg
1               5                   10                  15

Ala Cys Ile Ala Arg Tyr Ala Asn Ser Ser Gly Pro Ala Arg Ala Val
            20                  25                  30

Asp Thr Lys Ala Ala Pro
        35

<210> SEQ ID NO 32
<211> LENGTH: 44
<212> TYPE: PRT
<213> ORGANISM: Artificial Sequence
<220> FEATURE:
<223> OTHER INFORMATION: DAB24 44 mer fragment L-form

<400> SEQUENCE: 32

Ser Lys Trp Ser Trp Ser Ser Arg Trp Gly Ser Pro Gln Asp Lys Val
1               5                   10                  15

Glu Lys Thr Arg Ala Gly Cys Gly Gly Ser Pro Ser Ser Thr Asn Cys
            20                  25                  30

His Pro Tyr Thr Phe Ala Pro Pro Pro Gln Ala Gly
        35                  40

<210> SEQ ID NO 33
<211> LENGTH: 44
<212> TYPE: PRT
<213> ORGANISM: Artificial Sequence
<220> FEATURE:
<223> OTHER INFORMATION: DAB30 44 mer fragment L-form

<400> SEQUENCE: 33

Ser Gly Phe Trp Glu Phe Ser Arg Gly Leu Trp Asp Gly Glu Asn Arg
1               5                   10                  15

Lys Ser Val Arg Ser Gly Cys Gly Phe Arg Gly Ser Ser Ala Gln Gly
            20                  25                  30

Pro Cys Pro Val Thr Pro Ala Thr Ile Asp Lys His
        35                  40

<210> SEQ ID NO 34
<211> LENGTH: 44
```

```
<212> TYPE: PRT
<213> ORGANISM: Artificial Sequence
<220> FEATURE:
<223> OTHER INFORMATION: DAX15 44 mer fragment L-form

<400> SEQUENCE: 34

Ser Glu Ser Gly Arg Cys Arg Ser Val Ser Arg Trp Met Thr Thr Trp
 1               5                  10                  15

Gln Thr Gln Lys Gly Gly Cys Gly Ser Asn Val Ser Arg Gly Ser Pro
            20                  25                  30

Leu Asp Pro Ser His Gln Thr Gly His Ala Thr Thr
        35                  40

<210> SEQ ID NO 35
<211> LENGTH: 39
<212> TYPE: PRT
<213> ORGANISM: Artificial Sequence
<220> FEATURE:
<223> OTHER INFORMATION: DAX23 39 mer fragment L-form

<400> SEQUENCE: 35

Arg Glu Trp Arg Phe Ala Gly Pro Pro Leu Asp Leu Trp Ala Gly Pro
 1               5                  10                  15

Ser Leu Pro Ser Phe Asn Ala Ser Ser His Pro Arg Ala Leu Arg Thr
            20                  25                  30

Tyr Trp Ser Gln Arg Pro Arg
        35

<210> SEQ ID NO 36
<211> LENGTH: 44
<212> TYPE: PRT
<213> ORGANISM: Artificial Sequence
<220> FEATURE:
<223> OTHER INFORMATION: DAX24 44 mer fragment L-form

<400> SEQUENCE: 36

Arg Met Glu Asp Ile Lys Asn Ser Gly Trp Arg Asp Ser Cys Arg Trp
 1               5                  10                  15

Gly Asp Leu Arg Pro Gly Cys Gly Ser Arg Gln Trp Tyr Pro Ser Asn
            20                  25                  30

Met Arg Ser Ser Arg Asp Tyr Pro Ala Gly Gly His
        35                  40

<210> SEQ ID NO 37
<211> LENGTH: 36
<212> TYPE: PRT
<213> ORGANISM: Artificial Sequence
<220> FEATURE:
<223> OTHER INFORMATION: DAX27 36 mer fragment L-form

<400> SEQUENCE: 37

Ser His Pro Trp Tyr Arg His Trp Asn His Gly Asp Phe Ser Gly Ser
 1               5                  10                  15

Gly Gln Ser Arg His Thr Pro Pro Glu Ser Pro His Pro Gly Arg Pro
            20                  25                  30

Asn Ala Thr Ile
        35

<210> SEQ ID NO 38
<211> LENGTH: 44
<212> TYPE: PRT
<213> ORGANISM: Artificial Sequence
<220> FEATURE:
```

<223> OTHER INFORMATION: DCX8 44 mer fragment L-form

<400> SEQUENCE: 38

Arg Tyr Lys His Asp Ile Gly Cys Asp Ala Gly Val Asp Lys Ser
1               5                   10                  15

Ser Ser Val Arg Gly Gly Cys Gly Ala His Ser Ser Pro Arg Ala
                20                  25                  30

Gly Arg Gly Pro Arg Gly Thr Met Val Ser Arg Leu
            35                  40

<210> SEQ ID NO 39
<211> LENGTH: 44
<212> TYPE: PRT
<213> ORGANISM: Artificial Sequence
<220> FEATURE:
<223> OTHER INFORMATION: DCX11 44 mer fragment L-form

<400> SEQUENCE: 39

Ser Gln Gly Ser Lys Gln Cys Met Gln Tyr Arg Thr Gly Arg Leu Thr
1               5                   10                  15

Val Gly Ser Glu Tyr Gly Cys Gly Met Asn Pro Ala Arg His Ala Thr
                20                  25                  30

Pro Ala Tyr Pro Ala Arg Leu Leu Pro Arg Tyr Arg
            35                  40

<210> SEQ ID NO 40
<211> LENGTH: 44
<212> TYPE: PRT
<213> ORGANISM: Artificial Sequence
<220> FEATURE:
<223> OTHER INFORMATION: DCX26 44 mer fragment L-form

<400> SEQUENCE: 40

Ser Gly Arg Thr Thr Ser Glu Ile Ser Gly Leu Trp Gly Trp Gly Asp
1               5                   10                  15

Asp Arg Ser Gly Tyr Gly Trp Gly Asn Thr Leu Arg Pro Asn Tyr Ile
                20                  25                  30

Pro Tyr Arg Gln Ala Thr Asn Arg His Arg Tyr Thr
            35                  40

<210> SEQ ID NO 41
<211> LENGTH: 39
<212> TYPE: PRT
<213> ORGANISM: Artificial Sequence
<220> FEATURE:
<223> OTHER INFORMATION: DCX33 39 mer fragment L-form

<400> SEQUENCE: 41

Arg Trp Asn Trp Thr Val Leu Pro Ala Thr Gly Gly His Tyr Trp Thr
1               5                   10                  15

Arg Ser Thr Asp Tyr His Ala Ile Asn Asn His Arg Pro Ser Ile Pro
                20                  25                  30

His Gln His Pro Thr Pro Ile
            35

<210> SEQ ID NO 42
<211> LENGTH: 44
<212> TYPE: PRT
<213> ORGANISM: Artificial Sequence
<220> FEATURE:
<223> OTHER INFORMATION: DCX36 44 mer fragment L-form

<400> SEQUENCE: 42

```
Ser Trp Ser Ser Trp Asn Trp Ser Ser Lys Thr Thr Arg Leu Gly Asp
1               5                   10                  15

Arg Ala Thr Arg Glu Gly Cys Gly Pro Ser Gln Ser Asp Gly Cys Pro
                20                  25                  30

Tyr Asn Gly Arg Leu Thr Thr Val Lys Pro Arg Thr
            35                  40
```

<210> SEQ ID NO 43
<211> LENGTH: 37
<212> TYPE: PRT
<213> ORGANISM: Artificial Sequence
<220> FEATURE:
<223> OTHER INFORMATION: DCX39 37 mer fragment L-form

<400> SEQUENCE: 43

```
Ser Gly Ser Leu Asn Ala Trp Gln Pro Arg Ser Trp Val Gly Gly Ala
1               5                   10                  15

Phe Arg Ser His Ala Asn Asn Asn Leu Asn Pro Lys Pro Thr Met Val
                20                  25                  30

Thr Arg His Pro Thr
            35
```

<210> SEQ ID NO 44
<211> LENGTH: 44
<212> TYPE: PRT
<213> ORGANISM: Artificial Sequence
<220> FEATURE:
<223> OTHER INFORMATION: DCX42 44 mer fragment L-form

<400> SEQUENCE: 44

```
Arg Tyr Ser Gly Leu Ser Pro Arg Asp Asn Gly Pro Ala Cys Ser Gln
1               5                   10                  15

Glu Ala Thr Leu Glu Gly Cys Gly Ala Gln Arg Leu Met Ser Thr Arg
                20                  25                  30

Arg Lys Gly Arg Asn Ser Arg Pro Gly Trp Thr Leu
            35                  40
```

<210> SEQ ID NO 45
<211> LENGTH: 39
<212> TYPE: PRT
<213> ORGANISM: Artificial Sequence
<220> FEATURE:
<223> OTHER INFORMATION: DCX45 39 mer fragment L-form

<400> SEQUENCE: 45

```
Ser Val Gly Asn Asp Lys Thr Ser Arg Pro Val Ser Phe Tyr Gly Arg
1               5                   10                  15

Val Ser Asp Leu Trp Asn Ala Ser Leu Met Pro Lys Arg Thr Pro Ser
                20                  25                  30

Ser Lys Arg His Asp Asp Gly
            35
```

<210> SEQ ID NO 46
<211> LENGTH: 38
<212> TYPE: PRT
<213> ORGANISM: Artificial Sequence
<220> FEATURE:
<223> OTHER INFORMATION: PAX9 38 mer fragment L-form

<400> SEQUENCE: 46

```
Arg Trp Pro Ser Val Gly Tyr Lys Gly Asn Gly Ser Asp Thr Ile Asp
1               5                   10                  15
```

-continued

Val His Ser Asn Asp Ala Ser Thr Lys Arg Ser Leu Ile Tyr Asn His
            20                  25                  30

Arg Arg Pro Leu Phe Pro
        35

<210> SEQ ID NO 47
<211> LENGTH: 39
<212> TYPE: PRT
<213> ORGANISM: Artificial Sequence
<220> FEATURE:
<223> OTHER INFORMATION: PAX14 39 mer fragment L-form

<400> SEQUENCE: 47

Arg Thr Phe Glu Asn Asp Gly Leu Gly Val Gly Arg Ser Ile Gln Lys
1               5                   10                  15

Lys Ser Asp Arg Trp Tyr Ala Ser His Asn Ile Arg Ser His Phe Ala
            20                  25                  30

Ser Met Ser Pro Ala Gly Lys
        35

<210> SEQ ID NO 48
<211> LENGTH: 44
<212> TYPE: PRT
<213> ORGANISM: Artificial Sequence
<220> FEATURE:
<223> OTHER INFORMATION: PAX15 44 mer fragment L-form

<400> SEQUENCE: 48

Ser Tyr Cys Arg Val Lys Gly Gly Gly Glu Gly Gly His Thr Asp Ser
1               5                   10                  15

Asn Leu Ala Arg Ser Gly Cys Gly Lys Val Ala Arg Thr Ser Arg Leu
            20                  25                  30

Gln His Ile Asn Pro Arg Ala Thr Pro Pro Ser Arg
        35                  40

<210> SEQ ID NO 49
<211> LENGTH: 39
<212> TYPE: PRT
<213> ORGANISM: Artificial Sequence
<220> FEATURE:
<223> OTHER INFORMATION: PAX16 39 mer fragment L-form

<400> SEQUENCE: 49

Ser Trp Thr Arg Trp Gly Lys His Thr His Gly Gly Phe Val Asn Lys
1               5                   10                  15

Ser Pro Pro Gly Lys Asn Ala Thr Ser Pro Tyr Thr Asp Ala Gln Leu
            20                  25                  30

Pro Ser Asp Gln Gly Pro Pro
        35

<210> SEQ ID NO 50
<211> LENGTH: 44
<212> TYPE: PRT
<213> ORGANISM: Artificial Sequence
<220> FEATURE:
<223> OTHER INFORMATION: PAX17 44 mer fragment L-form

<400> SEQUENCE: 50

Ser Gln Val Asp Ser Phe Arg Asn Ser Phe Arg Trp Tyr Glu Pro Ser
1               5                   10                  15

Arg Ala Leu Cys His Gly Cys Gly Lys Arg Asp Thr Ser Thr Thr Arg
            20                  25                  30

Ile His Asn Ser Pro Ser Asp Ser Tyr Pro Thr Arg
            35                  40

<210> SEQ ID NO 51
<211> LENGTH: 39
<212> TYPE: PRT
<213> ORGANISM: Artificial Sequence
<220> FEATURE:
<223> OTHER INFORMATION: PAX18 39 mer fragment L-form

<400> SEQUENCE: 51

Ser Phe Leu Arg Phe Gln Ser Pro Arg Phe Glu Asp Tyr Ser Arg Thr
1               5                   10                  15

Ile Ser Arg Leu Arg Asn Ala Thr Asn Pro Ser Asn Val Ser Asp Ala
            20                  25                  30

His Asn Asn Arg Ala Leu Ala
            35

<210> SEQ ID NO 52
<211> LENGTH: 39
<212> TYPE: PRT
<213> ORGANISM: Artificial Sequence
<220> FEATURE:
<223> OTHER INFORMATION: PAX35 39 mer fragment L-form

<400> SEQUENCE: 52

Arg Ser Ile Thr Asp Gly Gly Leu Asn Glu Val Asp Leu Ser Ser Val
1               5                   10                  15

Ser Asn Val Leu Glu Asn Ala Asn Ser His Arg Ala Tyr Arg Lys His
            20                  25                  30

Arg Pro Thr Leu Lys Arg Pro
            35

<210> SEQ ID NO 53
<211> LENGTH: 44
<212> TYPE: PRT
<213> ORGANISM: Artificial Sequence
<220> FEATURE:
<223> OTHER INFORMATION: PAX38 44 mer fragment L-form

<400> SEQUENCE: 53

Ser Ser Lys Val Ser Ser Pro Arg Asp Pro Thr Val Pro Arg Lys Gly
1               5                   10                  15

Gly Asn Val Asp Tyr Gly Cys Gly His Arg Ser Ser Ala Arg Met Pro
            20                  25                  30

Thr Ser Ala Leu Ser Ser Ile Thr Lys Cys Tyr Thr
            35                  40

<210> SEQ ID NO 54
<211> LENGTH: 44
<212> TYPE: PRT
<213> ORGANISM: Artificial Sequence
<220> FEATURE:
<223> OTHER INFORMATION: PAX40 44 mer fragment L-form

<400> SEQUENCE: 54

Arg Ala Ser Thr Gln Gly Gly Arg Gly Val Ala Pro Glu Phe Gly Ala
1               5                   10                  15

Ser Val Leu Gly Arg Gly Cys Gly Ser Ala Thr Tyr Tyr Thr Asn Ser
            20                  25                  30

Thr Ser Cys Lys Asp Ala Met Gly His Asn Tyr Ser
            35                  40

<210> SEQ ID NO 55
<211> LENGTH: 39
<212> TYPE: PRT
<213> ORGANISM: Artificial Sequence
<220> FEATURE:
<223> OTHER INFORMATION: PAX43 39 mer fragment L-form

<400> SEQUENCE: 55

Arg Trp Cys Glu Lys His Lys Phe Thr Ala Ala Arg Cys Ser Ala Gly
1               5                   10                  15

Ala Gly Phe Glu Arg Asp Ala Ser Arg Pro Pro Gln Pro Ala His Arg
            20                  25                  30

Asp Asn Thr Asn Arg Asn Ala
        35

<210> SEQ ID NO 56
<211> LENGTH: 39
<212> TYPE: PRT
<213> ORGANISM: Artificial Sequence
<220> FEATURE:
<223> OTHER INFORMATION: PAX45 39 mer fragment L-form

<400> SEQUENCE: 56

Ser Phe Gln Val Tyr Pro Asp His Gly Leu Glu Arg His Ala Leu Asp
1               5                   10                  15

Gly Thr Gly Pro Leu Tyr Ala Met Pro Gly Arg Trp Leu Arg Ala Arg
            20                  25                  30

Pro Gln Asn Arg Asp Arg Gln
        35

<210> SEQ ID NO 57
<211> LENGTH: 38
<212> TYPE: PRT
<213> ORGANISM: Artificial Sequence
<220> FEATURE:
<223> OTHER INFORMATION: PAX46 38 mer fragment L-form

<400> SEQUENCE: 57

Ser Arg Cys Thr Asp Asn Glu Gln Cys Pro Asp Thr Gly Thr Arg Ser
1               5                   10                  15

Arg Ser Val Ser Asn Ala Arg Tyr Phe Ser Ser Arg Leu Leu Lys Thr
            20                  25                  30

His Ala Pro His Arg Pro
        35

<210> SEQ ID NO 58
<211> LENGTH: 39
<212> TYPE: PRT
<213> ORGANISM: Artificial Sequence
<220> FEATURE:
<223> OTHER INFORMATION: P31 39 mer fragment L-form

<400> SEQUENCE: 58

Ser Ala Arg Asp Ser Gly Pro Ala Glu Asp Gly Ser Arg Ala Val Arg
1               5                   10                  15

Leu Asn Gly Val Glu Asn Ala Asn Thr Arg Lys Ser Ser Arg Ser Asn
            20                  25                  30

Pro Arg Gly Arg Arg His Pro
        35

<210> SEQ ID NO 59

```
<211> LENGTH: 44
<212> TYPE: PRT
<213> ORGANISM: Artificial Sequence
<220> FEATURE:
<223> OTHER INFORMATION: P90 44 mer fragment L-form

<400> SEQUENCE: 59

Ser Ser Ala Asp Ala Glu Lys Cys Ala Gly Ser Leu Leu Trp Trp Gly
1               5                   10                  15

Arg Gln Asn Asn Ser Gly Cys Gly Ser Pro Thr Lys Lys His Leu Lys
            20                  25                  30

His Arg Asn Arg Ser Gln Thr Ser Ser Ser His
        35                  40

<210> SEQ ID NO 60
<211> LENGTH: 39
<212> TYPE: PRT
<213> ORGANISM: Artificial Sequence
<220> FEATURE:
<223> OTHER INFORMATION: 5PAX3 39 mer fragment L-form

<400> SEQUENCE: 60

Arg Pro Lys Asn Val Ala Asp Ala Tyr Ser Ser Gln Asp Gly Ala Ala
1               5                   10                  15

Ala Glu Glu Thr Ser His Ala Ser Asn Ala Ala Arg Lys Ser Pro Lys
            20                  25                  30

His Lys Pro Leu Arg Arg Pro
        35

<210> SEQ ID NO 61
<211> LENGTH: 39
<212> TYPE: PRT
<213> ORGANISM: Artificial Sequence
<220> FEATURE:
<223> OTHER INFORMATION: 5PAX5 39 mer fragment L-form

<400> SEQUENCE: 61

Arg Gly Ser Thr Gly Thr Ala Gly Gly Glu Arg Ser Gly Val Leu Asn
1               5                   10                  15

Leu His Thr Arg Asp Asn Ala Ser Gly Ser Gly Phe Lys Pro Trp Tyr
            20                  25                  30

Pro Ser Asn Arg Gly His Lys
        35

<210> SEQ ID NO 62
<211> LENGTH: 39
<212> TYPE: PRT
<213> ORGANISM: Artificial Sequence
<220> FEATURE:
<223> OTHER INFORMATION: 5PAX7 39 mer fragment L-form

<400> SEQUENCE: 62

Arg Trp Gly Trp Glu Arg Ser Pro Ser Asp Tyr Asp Ser Asp Met Asp
1               5                   10                  15

Leu Gly Ala Arg Arg Tyr Ala Thr Arg Thr His Arg Ala Pro Pro Arg
            20                  25                  30

Val Leu Lys Ala Pro Leu Pro
        35

<210> SEQ ID NO 63
<211> LENGTH: 44
<212> TYPE: PRT
<213> ORGANISM: Artificial Sequence
```

```
<220> FEATURE:
<223> OTHER INFORMATION: 5PAX12 44 mer fragment L-form

<400> SEQUENCE: 63

Arg Gly Trp Lys Cys Glu Gly Ser Gln Ala Ala Tyr Gly Asp Lys Asp
1               5                   10                  15

Ile Gly Arg Ser Arg Gly Cys Gly Ser Ile Thr Lys Asn Asn Thr Asn
            20                  25                  30

His Ala His Pro Ser His Gly Ala Val Ala Lys Ile
        35                  40

<210> SEQ ID NO 64
<211> LENGTH: 39
<212> TYPE: PRT
<213> ORGANISM: Artificial Sequence
<220> FEATURE:
<223> OTHER INFORMATION: HAX9 39 mer fragment L-form

<400> SEQUENCE: 64

Ser Arg Glu Glu Ala Asn Trp Asp Gly Tyr Lys Arg Glu Met Ser His
1               5                   10                  15

Arg Ser Arg Phe Trp Asp Ala Thr His Leu Ser Arg Pro Arg Arg Pro
            20                  25                  30

Ala Asn Ser Gly Asp Pro Asn
        35

<210> SEQ ID NO 65
<211> LENGTH: 44
<212> TYPE: PRT
<213> ORGANISM: Artificial Sequence
<220> FEATURE:
<223> OTHER INFORMATION: HAX35 44 mer fragment L-form

<400> SEQUENCE: 65

Glu Trp Tyr Ser Trp Lys Arg Ser Ser Lys Ser Thr Gly Leu Gly Asp
1               5                   10                  15

Thr Ala Thr Arg Glu Gly Cys Gly Pro Ser Gln Ser Asp Gly Cys Pro
            20                  25                  30

Tyr Asn Gly Arg Leu Thr Thr Val Lys Pro Arg Lys
        35                  40

<210> SEQ ID NO 66
<211> LENGTH: 44
<212> TYPE: PRT
<213> ORGANISM: Artificial Sequence
<220> FEATURE:
<223> OTHER INFORMATION: HAX40 44 mer fragment L-form

<400> SEQUENCE: 66

Arg Glu Phe Ala Glu Arg Arg Leu Trp Gly Cys Asp Asp Leu Ser Trp
1               5                   10                  15

Arg Leu Asp Ala Glu Gly Cys Gly Pro Thr Pro Ser Asn Arg Ala Val
            20                  25                  30

Lys His Arg Lys Pro Arg Pro Arg Ser Pro Ala Leu
        35                  40

<210> SEQ ID NO 67
<211> LENGTH: 44
<212> TYPE: PRT
<213> ORGANISM: Artificial Sequence
<220> FEATURE:
<223> OTHER INFORMATION: HAX42 44 mer fragment L-form
```

-continued

```
<400> SEQUENCE: 67

Ser Asp His Ala Leu Gly Thr Asn Leu Arg Ser Asp Asn Ala Lys Glu
1               5                   10                  15

Pro Gly Asp Tyr Asn Cys Cys Gly Asn Gly Asn Ser Thr Gly Arg Lys
            20                  25                  30

Val Phe Asn Arg Arg Arg Pro Ser Ala Ile Pro Thr
        35                  40

<210> SEQ ID NO 68
<211> LENGTH: 44
<212> TYPE: PRT
<213> ORGANISM: Artificial Sequence
<220> FEATURE:
<223> OTHER INFORMATION: HCA3 44 mer fragment L-form

<400> SEQUENCE: 68

Arg His Ile Ser Glu Tyr Ser Phe Ala Asn Ser His Leu Met Gly Gly
1               5                   10                  15

Glu Ser Lys Arg Lys Gly Cys Gly Ile Asn Gly Ser Phe Ser Pro Thr
            20                  25                  30

Cys Pro Arg Ser Pro Thr Pro Ala Phe Arg Arg Thr
        35                  40

<210> SEQ ID NO 69
<211> LENGTH: 38
<212> TYPE: PRT
<213> ORGANISM: Artificial Sequence
<220> FEATURE:
<223> OTHER INFORMATION: H40 38 mer fragment L-form

<400> SEQUENCE: 69

Ser Arg Glu Ser Gly Met Trp Gly Ser Trp Trp Arg Gly His Arg Leu
1               5                   10                  15

Asn Ser Thr Gly Gly Asn Ala Asn Met Asn Ala Ser Leu Pro Pro Asp
            20                  25                  30

Pro Pro Val Ser Thr Pro
        35

<210> SEQ ID NO 70
<211> LENGTH: 39
<212> TYPE: PRT
<213> ORGANISM: Artificial Sequence
<220> FEATURE:
<223> OTHER INFORMATION: PAX2 39 mer fragment L-form

<400> SEQUENCE: 70

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn Arg Arg Leu
            20                  25                  30

Arg Thr Arg Ser Arg Pro Asn
        35

<210> SEQ ID NO 71
<211> LENGTH: 1827
<212> TYPE: PRT
<213> ORGANISM: Artificial Sequence
<220> FEATURE:
<223> OTHER INFORMATION: hSI receptor

<400> SEQUENCE: 71

Met Ala Arg Lys Lys Phe Ser Gly Leu Glu Ile Ser Leu Ile Val Leu
```

-continued

```
1               5                   10                  15
Phe Val Ile Val Thr Ile Ile Ala Ile Ala Leu Ile Val Leu Ala
                20                  25                  30
Thr Lys Thr Pro Ala Val Asp Glu Ile Ser Asp Ser Thr Ser Thr Pro
                35                  40                      45
Ala Thr Thr Arg Val Thr Thr Asn Pro Ser Asp Ser Gly Lys Cys Pro
 50                  55                  60
Asn Val Leu Asn Asp Pro Val Asn Val Arg Ile Asn Cys Ile Pro Glu
 65                  70                  75                  80
Gln Phe Pro Thr Glu Gly Ile Cys Ala Gln Arg Gly Cys Cys Trp Arg
                    85                  90                  95
Pro Trp Asn Asp Ser Leu Ile Pro Trp Cys Phe Phe Val Asp Asn His
                100                 105                 110
Gly Tyr Asn Val Gln Asp Met Thr Thr Ser Ile Gly Val Glu Ala
                115                 120                 125
Lys Leu Asn Arg Ile Pro Ser Pro Thr Leu Phe Gly Asn Asp Ile Asn
                130                 135                 140
Ser Val Leu Phe Thr Thr Gln Asn Gln Thr Pro Asn Arg Phe Arg Phe
145                 150                 155                 160
Lys Ile Thr Asp Pro Asn Asn Arg Arg Tyr Glu Val Pro His Gln Tyr
                165                 170                 175
Val Lys Glu Phe Thr Gly Pro Thr Val Ser Asp Thr Leu Tyr Asp Val
                180                 185                 190
Lys Val Ala Gln Asn Pro Phe Ser Ile Gln Val Ile Arg Lys Ser Asn
                195                 200                 205
Gly Lys Thr Leu Phe Asp Thr Ser Ile Gly Pro Leu Val Tyr Ser Asp
                210                 215                 220
Gln Tyr Leu Gln Ile Ser Ala Arg Leu Pro Ser Asp Tyr Ile Tyr Gly
225                 230                 235                 240
Ile Gly Glu Gln Val His Lys Arg Phe Arg His Asp Leu Ser Trp Lys
                245                 250                 255
Thr Trp Pro Ile Phe Thr Arg Asp Gln Leu Pro Gly Asp Asn Asn Asn
                260                 265                 270
Asn Leu Tyr Gly His Gln Thr Phe Phe Met Cys Ile Glu Asp Thr Ser
                275                 280                 285
Gly Lys Ser Phe Gly Val Phe Leu Met Asn Ser Asn Ala Met Glu Ile
                290                 295                 300
Phe Ile Gln Pro Thr Pro Ile Val Thr Tyr Arg Val Thr Gly Gly Ile
305                 310                 315                 320
Leu Asp Phe Tyr Ile Leu Leu Gly Asp Thr Pro Glu Gln Val Val Gln
                325                 330                 335
Gln Tyr Gln Gln Leu Val Gly Leu Pro Ala Met Pro Ala Tyr Trp Asn
                340                 345                 350
Leu Gly Phe Gln Leu Ser Arg Trp Asn Tyr Lys Ser Leu Asp Val Val
                355                 360                 365
Lys Glu Val Val Arg Arg Asn Arg Glu Ala Gly Ile Pro Phe Asp Thr
                370                 375                 380
Gln Val Thr Asp Ile Asp Tyr Met Glu Asp Lys Lys Asp Phe Thr Tyr
385                 390                 395                 400
Asp Gln Val Ala Phe Asn Gly Leu Pro Gln Phe Val Gln Asp Leu His
                405                 410                 415
Asp His Gly Gln Lys Tyr Val Ile Ile Leu Asp Pro Ala Ile Ser Ile
                420                 425                 430
```

```
Gly Arg Arg Ala Asn Gly Thr Thr Tyr Ala Thr Tyr Glu Arg Gly Asn
            435                 440                 445

Thr Gln His Val Trp Ile Asn Glu Ser Asp Gly Ser Thr Pro Ile Ile
    450                 455                 460

Gly Glu Val Trp Pro Gly Leu Thr Val Tyr Pro Asp Phe Thr Asn Pro
465                 470                 475                 480

Asn Cys Ile Asp Trp Trp Ala Asn Glu Cys Ser Ile Phe His Gln Glu
                485                 490                 495

Val Gln Tyr Asp Gly Leu Trp Ile Asp Met Asn Glu Val Ser Ser Phe
            500                 505                 510

Ile Gln Gly Ser Thr Lys Gly Cys Asn Val Asn Lys Leu Asn Tyr Pro
        515                 520                 525

Pro Phe Thr Pro Asp Ile Leu Asp Lys Leu Met Tyr Ser Lys Thr Ile
    530                 535                 540

Cys Met Asp Ala Val Gln Asn Trp Gly Lys Gln Tyr Asp Val His Ser
545                 550                 555                 560

Leu Tyr Gly Tyr Ser Met Ala Ile Ala Thr Glu Gln Ala Val Gln Lys
                565                 570                 575

Val Phe Pro Asn Lys Arg Ser Phe Ile Leu Thr Arg Ser Thr Phe Ala
            580                 585                 590

Gly Ser Gly Arg His Ala Ala His Trp Leu Gly Asp Asn Thr Ala Ser
        595                 600                 605

Trp Glu Gln Met Glu Trp Ser Ile Thr Gly Met Leu Glu Phe Ser Leu
    610                 615                 620

Phe Gly Ile Pro Leu Val Gly Ala Asp Ile Cys Gly Phe Val Ala Glu
625                 630                 635                 640

Thr Thr Glu Glu Leu Cys Arg Arg Trp Met Gln Leu Gly Ala Phe Tyr
                645                 650                 655

Pro Phe Ser Arg Asn His Asn Ser Asp Gly Tyr Glu His Gln Asp Pro
            660                 665                 670

Ala Phe Phe Gly Gln Asn Ser Leu Leu Val Lys Ser Ser Arg Gln Tyr
        675                 680                 685

Leu Thr Ile Arg Tyr Thr Leu Leu Pro Phe Leu Tyr Thr Leu Phe Tyr
    690                 695                 700

Lys Ala His Val Phe Gly Glu Thr Val Ala Arg Pro Val Leu His Glu
705                 710                 715                 720

Phe Tyr Glu Asp Thr Asn Ser Trp Ile Glu Asp Thr Glu Phe Leu Trp
                725                 730                 735

Gly Pro Ala Leu Leu Ile Thr Pro Val Leu Lys Gln Gly Ala Asp Thr
            740                 745                 750

Val Ser Ala Tyr Ile Pro Asp Ala Ile Trp Tyr Asp Tyr Glu Ser Gly
        755                 760                 765

Ala Lys Arg Pro Trp Arg Lys Gln Arg Val Asp Met Tyr Leu Pro Ala
    770                 775                 780

Asp Lys Ile Gly Leu His Leu Arg Gly Gly Tyr Ile Ile Pro Ile Gln
785                 790                 795                 800

Glu Pro Asp Val Thr Thr Thr Ala Ser Arg Lys Asn Pro Leu Gly Leu
                805                 810                 815

Ile Val Ala Leu Gly Glu Asn Asn Thr Ala Lys Gly Asp Phe Phe Trp
            820                 825                 830

Asp Asp Gly Glu Thr Lys Asp Thr Ile Gln Asn Gly Asn Tyr Ile Leu
        835                 840                 845
```

-continued

```
Tyr Thr Phe Ser Val Ser Asn Asn Thr Leu Asp Ile Val Cys Thr His
850                 855                 860

Ser Ser Tyr Gln Glu Gly Thr Thr Leu Ala Phe Gln Thr Val Lys Ile
865                 870                 875                 880

Leu Gly Leu Thr Asp Ser Val Thr Glu Val Arg Val Ala Glu Asn Asn
                885                 890                 895

Gln Pro Met Asn Ala His Ser Asn Phe Thr Tyr Asp Ala Ser Asn Gln
            900                 905                 910

Val Leu Leu Ile Ala Asp Leu Lys Leu Asn Leu Gly Arg Asn Phe Ser
        915                 920                 925

Val Gln Trp Asn Gln Ile Phe Ser Glu Asn Glu Arg Phe Asn Cys Tyr
    930                 935                 940

Pro Asp Ala Asp Leu Ala Thr Glu Gln Lys Cys Thr Gln Arg Gly Cys
945                 950                 955                 960

Val Trp Arg Thr Gly Ser Ser Leu Ser Lys Ala Pro Glu Cys Tyr Phe
                965                 970                 975

Pro Arg Gln Asp Asn Ser Tyr Ser Val Asn Ser Ala Arg Tyr Ser Ser
            980                 985                 990

Met Gly Ile Thr Ala Asp Leu Gln  Leu Asn Thr Ala Asn  Ala Arg Ile
        995                 1000                1005

Lys Leu  Pro Ser Asp Pro Ile  Ser Thr Leu Arg Val  Glu Val Lys
    1010                1015                1020

Tyr His  Lys Asn Asp Met Leu  Gln Phe Lys Ile Tyr  Asp Pro Gln
    1025                1030                1035

Lys Lys  Arg Tyr Glu Val Pro  Val Pro Leu Asn Ile  Pro Thr Thr
    1040                1045                1050

Pro Ile  Ser Thr Tyr Glu Asp  Arg Leu Tyr Asp Val  Glu Ile Lys
    1055                1060                1065

Glu Asn  Pro Phe Gly Ile Gln  Ile Arg Arg Arg Ser  Ser Gly Arg
    1070                1075                1080

Val Ile  Trp Asp Ser Trp Leu  Pro Gly Phe Ala Phe  Asn Asp Gln
    1085                1090                1095

Phe Ile  Gln Ile Ser Thr Arg  Leu Pro Ser Glu Tyr  Ile Tyr Gly
    1100                1105                1110

Phe Gly  Glu Val Glu His Thr  Ala Phe Lys Arg Asp  Leu Asn Trp
    1115                1120                1125

Asn Thr  Trp Gly Met Phe Thr  Arg Asp Gln Pro Pro  Gly Tyr Lys
    1130                1135                1140

Leu Asn  Ser Tyr Gly Phe His  Pro Tyr Tyr Met Ala  Leu Glu Glu
    1145                1150                1155

Glu Gly  Asn Ala His Gly Val  Phe Leu Leu Asn Ser  Asn Ala Met
    1160                1165                1170

Asp Val  Thr Phe Gln Pro Thr  Pro Ala Leu Thr Tyr  Arg Thr Val
    1175                1180                1185

Gly Gly  Ile Leu Asp Phe Tyr  Met Phe Leu Gly Pro  Thr Pro Gln
    1190                1195                1200

Val Ala  Thr Lys Gln Tyr His  Glu Val Ile Gly His  Pro Val Met
    1205                1210                1215

Pro Ala  Tyr Trp Ala Leu Gly  Phe Gln Leu Cys Arg  Tyr Gly Tyr
    1220                1225                1230

Ala Asn  Thr Ser Glu Val Arg  Glu Leu Tyr Asp Ala  Met Val Ala
    1235                1240                1245

Ala Asn  Ile Pro Tyr Asp Val  Gln Tyr Thr Asp Ile  Asp Tyr Met
```

```
                    1250                    1255                    1260

Glu Arg Gln Leu Asp Phe Thr Ile Gly Glu Ala Phe Gln Asp Leu
    1265                    1270                    1275

Pro Gln Phe Val Asp Lys Ile Arg Gly Glu Gly Met Arg Tyr Ile
    1280                    1285                    1290

Ile Ile Leu Asp Pro Ala Ile Ser Gly Asn Glu Thr Lys Thr Tyr
    1295                    1300                    1305

Pro Ala Phe Glu Arg Gly Gln Gln Asn Asp Val Phe Val Lys Trp
    1310                    1315                    1320

Pro Asn Thr Asn Asp Ile Cys Trp Ala Lys Val Trp Pro Asp Leu
    1325                    1330                    1335

Pro Asn Ile Thr Ile Asp Lys Thr Leu Thr Glu Asp Glu Ala Val
    1340                    1345                    1350

Asn Ala Ser Arg Ala His Val Ala Phe Pro Asp Phe Phe Arg Thr
    1355                    1360                    1365

Ser Thr Ala Glu Trp Trp Ala Arg Glu Ile Val Asp Phe Tyr Asn
    1370                    1375                    1380

Glu Lys Met Lys Phe Asp Gly Leu Trp Ile Asp Met Asn Glu Pro
    1385                    1390                    1395

Ser Ser Phe Val Asn Gly Thr Thr Thr Asn Gln Cys Arg Asn Asp
    1400                    1405                    1410

Glu Leu Asn Tyr Pro Pro Tyr Phe Pro Glu Leu Thr Lys Arg Thr
    1415                    1420                    1425

Asp Gly Leu His Phe Arg Thr Ile Cys Met Glu Ala Glu Gln Ile
    1430                    1435                    1440

Leu Ser Asp Gly Thr Ser Val Leu His Tyr Asp Val His Asn Leu
    1445                    1450                    1455

Tyr Gly Trp Ser Gln Met Lys Pro Thr His Asp Ala Leu Gln Lys
    1460                    1465                    1470

Thr Thr Gly Lys Arg Gly Ile Val Ile Ser Arg Ser Thr Tyr Pro
    1475                    1480                    1485

Thr Ser Gly Arg Trp Gly Gly His Trp Leu Gly Asp Asn Tyr Ala
    1490                    1495                    1500

Arg Trp Asp Asn Met Asp Lys Ser Ile Ile Gly Met Met Glu Phe
    1505                    1510                    1515

Ser Leu Phe Gly Ile Ser Tyr Thr Gly Ala Asp Ile Cys Gly Phe
    1520                    1525                    1530

Phe Asn Asn Ser Glu Tyr His Leu Cys Thr Arg Trp Met Gln Leu
    1535                    1540                    1545

Gly Ala Phe Tyr Pro Tyr Ser Arg Asn His Asn Ile Ala Asn Thr
    1550                    1555                    1560

Arg Arg Gln Asp Pro Ala Ser Trp Asn Glu Thr Phe Ala Glu Met
    1565                    1570                    1575

Ser Arg Asn Ile Leu Asn Ile Arg Tyr Thr Leu Leu Pro Tyr Phe
    1580                    1585                    1590

Tyr Thr Gln Met His Glu Ile His Ala Asn Gly Gly Thr Val Ile
    1595                    1600                    1605

Arg Pro Leu Leu His Glu Phe Phe Asp Glu Lys Pro Thr Trp Asp
    1610                    1615                    1620

Ile Phe Lys Gln Phe Leu Trp Gly Pro Ala Phe Met Val Thr Pro
    1625                    1630                    1635

Val Leu Glu Pro Tyr Val Gln Thr Val Asn Ala Tyr Val Pro Asn
    1640                    1645                    1650
```

-continued

```
Ala Arg Trp Phe Asp Tyr His Thr Gly Lys Asp Ile Gly Val Arg
    1655                1660                1665

Gly Gln Phe Gln Thr Phe Asn Ala Ser Tyr Asp Thr Ile Asn Leu
    1670                1675                1680

His Val Arg Gly Gly His Ile Leu Pro Cys Gln Glu Pro Ala Gln
    1685                1690                1695

Asn Thr Phe Tyr Ser Arg Gln Lys His Met Lys Leu Ile Val Ala
    1700                1705                1710

Ala Asp Asp Asn Gln Met Ala Gln Gly Ser Leu Phe Trp Asp Asp
    1715                1720                1725

Gly Glu Ser Ile Asp Thr Tyr Glu Arg Asp Leu Tyr Leu Ser Val
    1730                1735                1740

Gln Phe Asn Leu Asn Gln Thr Thr Leu Thr Ser Thr Ile Leu Lys
    1745                1750                1755

Arg Gly Tyr Ile Asn Lys Ser Glu Thr Arg Leu Gly Ser Leu His
    1760                1765                1770

Val Trp Gly Lys Gly Thr Thr Pro Val Asn Ala Val Thr Leu Thr
    1775                1780                1785

Tyr Asn Gly Asn Lys Asn Ser Leu Pro Phe Asn Glu Asp Thr Thr
    1790                1795                1800

Asn Met Ile Leu Arg Ile Asp Leu Thr Thr His Asn Val Thr Leu
    1805                1810                1815

Glu Glu Pro Ile Glu Ile Asn Trp Ser
    1820                1825

<210> SEQ ID NO 72
<211> LENGTH: 685
<212> TYPE: PRT
<213> ORGANISM: Artificial Sequence
<220> FEATURE:
<223> OTHER INFORMATION: D2H receptor

<400> SEQUENCE: 72

Met Ala Glu Asp Lys Ser Lys Arg Asp Ser Ile Glu Met Ser Met Lys
1               5                   10                  15

Gly Cys Gln Thr Asn Asn Gly Phe Val His Asn Glu Asp Ile Leu Glu
            20                  25                  30

Gln Thr Pro Asp Pro Gly Ser Ser Thr Asp Asn Leu Lys His Ser Thr
        35                  40                  45

Arg Gly Ile Leu Gly Ser Gln Glu Pro Asp Phe Lys Gly Val Gln Pro
    50                  55                  60

Tyr Ala Gly Met Pro Lys Glu Val Leu Phe Gln Phe Ser Gly Gln Ala
65                  70                  75                  80

Arg Tyr Arg Ile Pro Arg Glu Ile Leu Phe Trp Leu Thr Val Ala Ser
                85                  90                  95

Val Leu Val Leu Ile Ala Ala Thr Ile Ala Ile Ile Ala Leu Ser Pro
            100                 105                 110

Lys Cys Leu Asp Trp Trp Gln Glu Gly Pro Met Tyr Gln Ile Tyr Pro
        115                 120                 125

Arg Ser Phe Lys Asp Ser Asn Lys Asp Gly Asn Gly Asp Leu Lys Gly
    130                 135                 140

Ile Gln Asp Lys Leu Asp Tyr Ile Thr Ala Leu Asn Ile Lys Thr Val
145                 150                 155                 160

Trp Ile Thr Ser Phe Tyr Lys Ser Leu Lys Asp Phe Arg Tyr Gly
                165                 170                 175
```

```
Val Glu Asp Phe Arg Glu Val Asp Pro Ile Phe Gly Thr Met Glu Asp
            180                 185                 190

Phe Glu Asn Leu Val Ala Ala Ile His Asp Lys Gly Leu Lys Leu Ile
            195                 200                 205

Ile Asp Phe Ile Pro Asn His Thr Ser Asp Lys His Ile Trp Phe Gln
            210                 215                 220

Leu Ser Arg Thr Arg Thr Gly Lys Tyr Thr Asp Tyr Tyr Ile Trp His
225                 230                 235                 240

Asp Cys Thr His Glu Asn Gly Lys Thr Ile Pro Pro Asn Asn Trp Leu
                245                 250                 255

Ser Val Tyr Gly Asn Ser Ser Trp His Phe Asp Glu Val Arg Asn Gln
            260                 265                 270

Cys Tyr Phe His Gln Phe Met Lys Glu Gln Pro Asp Leu Asn Phe Arg
            275                 280                 285

Asn Pro Asp Val Gln Glu Ile Lys Glu Ile Leu Arg Phe Trp Leu
            290                 295                 300

Thr Lys Gly Val Asp Gly Phe Ser Leu Asp Ala Val Lys Phe Leu Leu
305                 310                 315                 320

Glu Ala Lys His Leu Arg Asp Glu Ile Gln Val Asn Lys Thr Gln Ile
                325                 330                 335

Pro Asp Thr Val Thr Gln Tyr Ser Glu Leu Tyr His Asp Phe Thr Thr
            340                 345                 350

Thr Gln Val Gly Met His Asp Ile Val Arg Ser Phe Arg Gln Thr Met
            355                 360                 365

Asp Gln Tyr Ser Thr Glu Pro Gly Arg Tyr Arg Phe Met Gly Thr Glu
370                 375                 380

Ala Tyr Ala Glu Ser Ile Asp Arg Thr Val Met Tyr Tyr Gly Leu Pro
385                 390                 395                 400

Phe Ile Gln Glu Ala Asp Phe Pro Phe Asn Asn Tyr Leu Ser Met Leu
            405                 410                 415

Asp Thr Val Ser Gly Asn Ser Val Tyr Glu Val Ile Thr Ser Trp Met
            420                 425                 430

Glu Asn Met Pro Glu Gly Lys Trp Pro Asn Trp Met Ile Gly Gly Pro
            435                 440                 445

Asp Ser Ser Arg Leu Thr Ser Arg Leu Gly Asn Gln Tyr Val Asn Val
450                 455                 460

Met Asn Met Leu Leu Phe Thr Leu Pro Gly Thr Pro Ile Thr Tyr Tyr
465                 470                 475                 480

Gly Glu Glu Ile Gly Met Gly Asn Ile Val Ala Ala Asn Leu Asn Glu
                485                 490                 495

Ser Tyr Asp Ile Asn Thr Leu Arg Ser Lys Ser Pro Met Gln Trp Asp
            500                 505                 510

Asn Ser Ser Asn Ala Gly Phe Ser Glu Ala Ser Asn Thr Trp Leu Pro
            515                 520                 525

Thr Asn Ser Asp Tyr His Thr Val Asn Val Asp Val Gln Lys Thr Gln
            530                 535                 540

Pro Arg Ser Ala Leu Lys Leu Tyr Gln Asp Leu Ser Leu Leu His Ala
545                 550                 555                 560

Asn Glu Leu Leu Leu Asn Arg Gly Trp Phe Cys His Leu Arg Asn Asp
                565                 570                 575

Ser His Tyr Val Val Tyr Thr Arg Glu Leu Asp Gly Ile Asp Arg Ile
            580                 585                 590
```

```
Phe Ile Val Val Leu Asn Phe Gly Glu Ser Thr Leu Leu Asn Leu His
            595                 600                 605

Asn Met Ile Ser Gly Leu Pro Ala Lys Ile Arg Ile Arg Leu Ser Thr
        610                 615                 620

Asn Ser Ala Asp Lys Gly Ser Lys Val Asp Thr Ser Gly Ile Phe Leu
625                 630                 635                 640

Asp Lys Gly Glu Gly Leu Ile Phe Glu His Asn Thr Lys Asn Leu Leu
                645                 650                 655

His Arg Gln Thr Ala Phe Arg Asp Arg Cys Phe Val Ser Asn Arg Ala
            660                 665                 670

Cys Tyr Ser Ser Val Leu Asn Ile Leu Tyr Thr Ser Cys
            675                 680                 685

<210> SEQ ID NO 73
<211> LENGTH: 11
<212> TYPE: PRT
<213> ORGANISM: Artificial Sequence
<220> FEATURE:
<223> OTHER INFORMATION: binding 11 mer fragment L-form
<220> FEATURE:
<221> NAME/KEY: MISC_FEATURE
<222> LOCATION: (1)..(1)
<223> OTHER INFORMATION: "Xaa"=Ser or Thr
<220> FEATURE:
<221> NAME/KEY: MISC_FEATURE
<222> LOCATION: (3)..(3)
<223> OTHER INFORMATION: "Xaa"=Arg or Lys
<220> FEATURE:
<221> NAME/KEY: MISC_FEATURE
<222> LOCATION: (4)..(4)
<223> OTHER INFORMATION: "Xaa"=Lys or Arg
<220> FEATURE:
<221> NAME/KEY: MISC_FEATURE
<222> LOCATION: (6)..(6)
<223> OTHER INFORMATION: "Xaa"=Ser or Leu
<220> FEATURE:
<221> NAME/KEY: MISC_FEATURE
<222> LOCATION: (7)..(7)
<223> OTHER INFORMATION: "Xaa"=Arg, Ile, Val, or Ser
<220> FEATURE:
<221> NAME/KEY: MISC_FEATURE
<222> LOCATION: (8)..(8)
<223> OTHER INFORMATION: "Xaa"=Ser, Tyr, Phe, or His
<220> FEATURE:
<221> NAME/KEY: MISC_FEATURE
<222> LOCATION: (10)..(10)
<223> OTHER INFORMATION: "Xaa"=Phe, His, or Arg

<400> SEQUENCE: 73

Xaa Thr Xaa Xaa Ser Xaa Xaa Xaa Asn Xaa Arg
1               5                   10

<210> SEQ ID NO 74
<211> LENGTH: 8
<212> TYPE: PRT
<213> ORGANISM: Artificial Sequence
<220> FEATURE:
<223> OTHER INFORMATION: binding 8 mer fragment L-form
<220> FEATURE:
<221> NAME/KEY: MISC_FEATURE
<222> LOCATION: (2)..(2)
<223> OTHER INFORMATION: "Xaa"=Ser, Ala, or Gly
<220> FEATURE:
<221> NAME/KEY: MISC_FEATURE
<222> LOCATION: (4)..(4)
<223> OTHER INFORMATION: "Xaa"=Val or Glu
<220> FEATURE:
<221> NAME/KEY: MISC_FEATURE
<222> LOCATION: (7)..(7)
<223> OTHER INFORMATION: "Xaa"= Pro, Gly, or Ser
<220> FEATURE:
```

<221> NAME/KEY: MISC_FEATURE
<222> LOCATION: (8)..(8)
<223> OTHER INFORMATION: "Xaa" = Trp or Tyr

<400> SEQUENCE: 74

Asp Xaa Asp Xaa Arg Arg Xaa Xaa
1               5

<210> SEQ ID NO 75
<211> LENGTH: 10
<212> TYPE: PRT
<213> ORGANISM: Artificial Sequence
<220> FEATURE:
<223> OTHER INFORMATION: binding 10 mer fragment L-form
<220> FEATURE:
<221> NAME/KEY: MISC_FEATURE
<222> LOCATION: (7)..(7)
<223> OTHER INFORMATION: "Xaa"=Ala or Phe
<220> FEATURE:
<221> NAME/KEY: MISC_FEATURE
<222> LOCATION: (8)..(8)
<223> OTHER INFORMATION: "Xaa"=Arg or His

<400> SEQUENCE: 75

Val Arg Ser Gly Cys Gly Xaa Xaa Ser Ser
1               5                   10

<210> SEQ ID NO 76
<211> LENGTH: 11
<212> TYPE: PRT
<213> ORGANISM: Artificial Sequence
<220> FEATURE:
<223> OTHER INFORMATION: binding 11 mer fragment L-form

<400> SEQUENCE: 76

Asn Thr Arg Lys Ser Ser Arg Ser Asn Pro Arg
1               5                   10

<210> SEQ ID NO 77
<211> LENGTH: 11
<212> TYPE: PRT
<213> ORGANISM: Artificial Sequence
<220> FEATURE:
<223> OTHER INFORMATION: binding 11 mer fragment L-form

<400> SEQUENCE: 77

Ser Thr Lys Arg Ser Leu Ile Tyr Asn His Arg
1               5                   10

<210> SEQ ID NO 78
<211> LENGTH: 10
<212> TYPE: PRT
<213> ORGANISM: Artificial Sequence
<220> FEATURE:
<223> OTHER INFORMATION: binding 10 mer fragment L-form

<400> SEQUENCE: 78

Ser Thr Gly Arg Lys Val Phe Asn Arg Arg
1               5                   10

<210> SEQ ID NO 79
<211> LENGTH: 11
<212> TYPE: PRT
<213> ORGANISM: Artificial Sequence
<220> FEATURE:
<223> OTHER INFORMATION: binding 11 mer fragment L-form

<400> SEQUENCE: 79

```
Thr Asn Ala Lys His Ser Ser His Asn Arg Arg
1               5                   10
```

<210> SEQ ID NO 80
<211> LENGTH: 8
<212> TYPE: PRT
<213> ORGANISM: Artificial Sequence
<220> FEATURE:
<223> OTHER INFORMATION: binding 8 mer fragment L-form

<400> SEQUENCE: 80

```
Asp Ser Asp Val Arg Arg Pro Trp
1               5
```

<210> SEQ ID NO 81
<211> LENGTH: 8
<212> TYPE: PRT
<213> ORGANISM: Artificial Sequence
<220> FEATURE:
<223> OTHER INFORMATION: binding 8 mer fragment L-form

<400> SEQUENCE: 81

```
Ala Ala Asp Gln Arg Arg Gly Trp
1               5
```

<210> SEQ ID NO 82
<211> LENGTH: 8
<212> TYPE: PRT
<213> ORGANISM: Artificial Sequence
<220> FEATURE:
<223> OTHER INFORMATION: binding 8 mer fragment L-form

<400> SEQUENCE: 82

```
Asp Gly Arg Gly Gly Arg Ser Tyr
1               5
```

<210> SEQ ID NO 83
<211> LENGTH: 4
<212> TYPE: PRT
<213> ORGANISM: Artificial Sequence
<220> FEATURE:
<223> OTHER INFORMATION: binding 4 mer fragment L-form

<400> SEQUENCE: 83

```
Arg Val Arg Ser
1
```

<210> SEQ ID NO 84
<211> LENGTH: 12
<212> TYPE: PRT
<213> ORGANISM: Artificial Sequence
<220> FEATURE:
<223> OTHER INFORMATION: binding 12 mer fragment L-form

<400> SEQUENCE: 84

```
Ser Val Arg Ser Gly Cys Gly Phe Arg Gly Ser Ser
1               5                   10
```

<210> SEQ ID NO 85
<211> LENGTH: 11
<212> TYPE: PRT
<213> ORGANISM: Artificial Sequence

```
-continued

<220> FEATURE:
<223> OTHER INFORMATION: binding 11 mer fragment L-form

<400> SEQUENCE: 85

Ser Val Arg Gly Gly Cys Gly Ala His Ser Ser
1               5                   10
```

US 7,491,796 B1

RETRO-INVERSION PEPTIDES THAT TARGET GIT RECEPTORS AND RELATED METHODS

CROSS-REFERENCE TO RELATED APPLICATIONS

This application claims priority to U.S. Provisional Application No. 60/109,038, filed Nov. 19, 1998, the disclosure of which is incorporated herein by reference.

FIELD OF THE INVENTION

The present invention relates generally to peptides that are capable of targeting or specifically binding to gastro-intestinal tract (GIT) transport receptors. In particular, this invention relates to retro-inverted forms of peptide sequences and motifs, as well as derivatives thereof, which enhance drug delivery and transport through tissue, such as epithelial cells lining the lumenal side of the GIT. Production of peptides and antibodies is also provided. The invention further relates to pharmaceutical compositions, formulations and related methods.

BACKGROUND OF THE INVENTION

Proteases cleave peptide bonds between adjacent L-amino acids, rendering these peptides susceptible to degradation in the GIT. Artificial proteins or peptides composed of D-amino acids are largely resistant to proteolytic breakdown. However, when D-amino acids are substituted for all L-amino acids in a peptide/protein, the corresponding D-peptide/protein is a mirror image of the original peptide/protein and is likely to have modified or lost biological activity because of this change in conformation. Retro-inverted peptides are peptides having all D-amino acids but are synthesized in the reverse order or sequence compared to the original L-peptide/protein. The carboxy terminus of the original peptide/protein becomes the amino terminus (and vice versa) of the retro-inverted peptide/protein and the resulting side chain surface of the retro-inverted peptide/protein is similar to the original L-peptide/protein. The net result of combining D-enantiomers and reverse synthesis is that the positions of carbonyl and amine groups in each amide bond are exchanged while the position of side-chain groups is preserved (Brady, L. and Dodson, G., *Nature,* 368L:692-693 (1994); Jameson et al., *Nature,* 368; 744-746 (1994)). This alteration in the protein backbone is self compensating in that hydrogen-bond donors become hydrogen-bond acceptors (amide carbonyl groups) and vice-versa. When the position of the side-chains relative to the backbone are unchanged the modified surface of the retro-inverted peptide/protein is largely unaltered compared to the original L-peptide/protein.

Previously, as disclosed and claimed in WO 98/51325, which is hereby incorporated by reference in its entirety, we have identified random peptides and their fragments, motifs, derivatives, analogs or peptidomimetics thereof which are capable of specific binding to GIT transport receptors such as the D2H (human D2 clone), hSI (human sucrase isomaltose), HPT1 (human intestinal oligopeptide transporter) and hPEPT1 (human oligopeptide transporter) receptors (hereinafter "GIT targeting agents"). These GIT targeting agents are capable of facilitating transport of an active agent through a human or animal gastro-intestinal tissue and have use, for example, in facilitating transport of active agents from the lumenal side of the GIT into the systemic blood system and/or in targeting active agents to the GIT. Thus, for example, by binding (covalently or noncovalently) the GIT targeting agent to an orally administered active agent, the active agent can be targeted to specific receptor sites or transport pathways which are known to operate in the human gastrointestinal tract, thus facilitating its absorption into the systemic system. Preferably, the active agent is a drug or a drug-containing nano- or microparticle.

SUMMARY OF THE INVENTION

Surprisingly, we have found that retro-inverted forms of the GIT targeting agents target specific receptor sites in vivo and/or promote uptake of active agents and/or enhance active agent delivery across the GIT into the systemic circulation. By using retro-inversion D-peptide synthesis, we have discovered retro-inverted D-peptides of the GIT targeting agents that retain the same function of the GIT targeting agents but have enhanced stability to proteases in the human or animal GIT. These retro-inverted peptides and compositions containing these retro-inverted peptides can be used to deliver an active agent, such as a drug or a drug-containing nano- or microparticle for treatment of a condition in a subject in need of the drug, in vivo by any of the uses or methods disclosed in the above-referenced WO 98/51325. Additionally, the invention provides antibodies which are capable of immunospecifically binding the retro-inverted peptides of this invention.

DETAILED DESCRIPTION OF THE INVENTION

Figure 1:
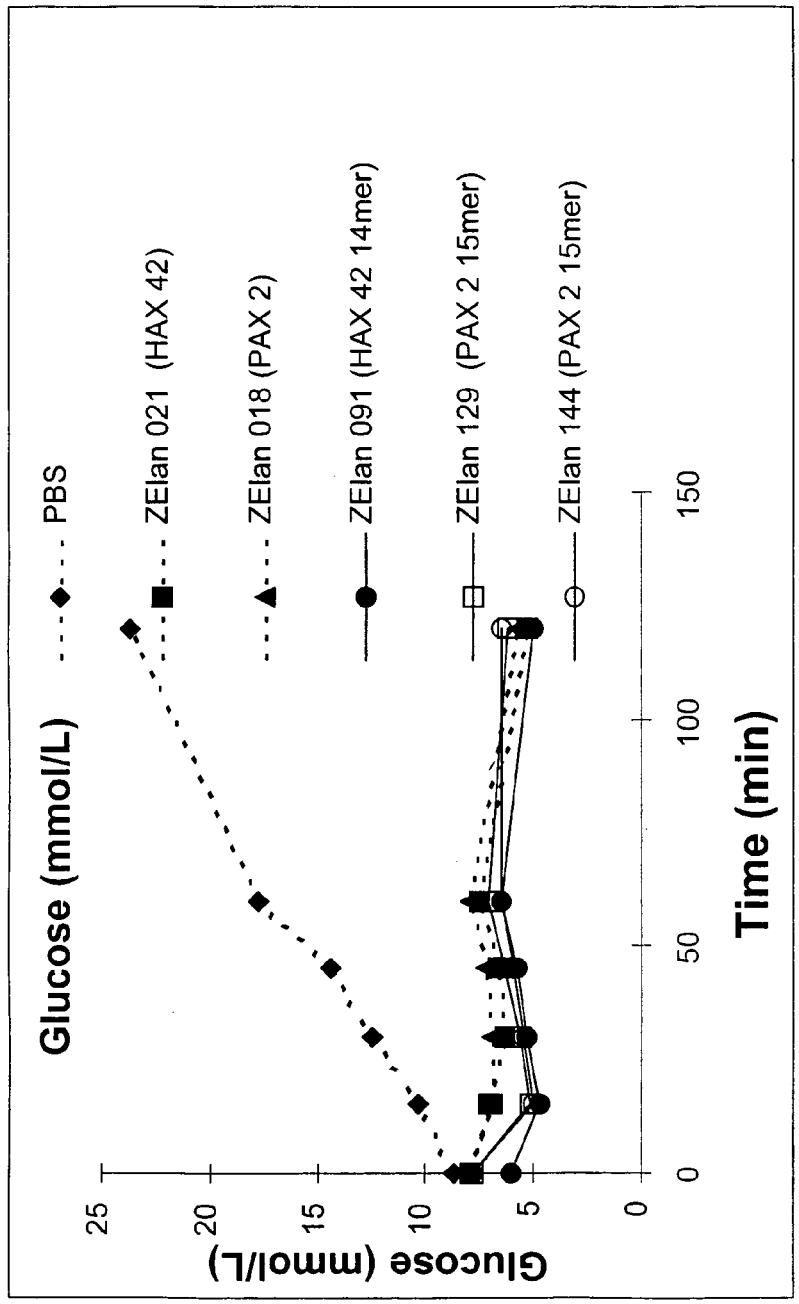
FIG. 1 shows the systemic blood glucose levels following intestinal administration of control (PBS); ZElan 021 coated insulin-containing particles, ZElan 018 coated insulin-containing particles, ZElan091 coated insulin-containing particles, ZElan129 coated insulin-containing particles and ZElan 144 coated insulin-containing particles according to this invention (300 iu insulin loading)

The present invention relates to retro-inverted peptides (also referred to herein as "targeting retro-inverted peptides" or "targeting retro-inversion peptides") that target specific receptor sites in vivo and/or promote uptake of active agents and/or enhance active agent delivery across the GIT into the systemic, portal or hepatic circulation. In particular, these retro-inverted peptides specifically bind to one or more of the human gastro-intestinal tract receptors HPT1, HPEPT1, D2H or hSI (for example, amino acids 29-273 of HPT1, amino acids 391-571 of HPEPT1, amino acids 387-685 of D2H, or amino acids 272-667 of hSI) or their equivalents in other mammals and have general utility in targeting active agents to selected sites and/or selected tissues in the body in which the receptors are expressed. These peptides are synthesized from D-amino acids and have a reverse sequence order of the GIT targeting agents disclosed and claimed in the above-referenced WO 98151325. The present invention also relates to derivatives (including but not limited to fragments) of these retro-inverted peptides, which derivatives are functionally similar to the retro-inverted peptides (that is, capable of displaying one or more known functional activities of the retro-inverted peptides). These functional activities include but are not limited to the ability to bind or to compete with binding to the gastro-intestinal tract receptors HPT1, HPEPT1, D2H or hSI or the ability to be bound by an antibody directed against the retro-inverted peptide. Derivatives can be tested for the desired activity by procedures known in the art, including binding to a receptor domain or to Caco-2 cells, in vitro, or to intestinal tissue, in vitro or in vivo.

Derivatives can be made by altering the retro-inverted peptides sequences by substitutions, additions or deletions that provide for functionally equivalent activity. Derivatives include, but are not limited to, those containing, as a primary amino acid sequence, all or part of the amino acid sequence of the retro-inverted peptide including altered sequences in which functionally equivalent amino acid residues are substituted for residues within the sequences resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Included within the scope of the invention are retro-inverted peptides or derivatives which are modified. e.g., by glycosoylation, acetylation, phosphorylation, amidation, derivation by known protecting/blocking groups, proteolytic cleavage, linkage to an antibody molecule or other cellular ligand, etc. Any of numerous chemical modifications may be carried out by known techniques. In a specific embodiment, the amino- and/or carboxy-termini are modified. Furthermore, is desired, nonclassical amino acids or chemical amino acid analogs can be introduced as a substitution or addition into the retro-inverted peptides sequence. Non-classical amino acids include but are not limited to α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In certain embodiments the peptides of the present invention are no more than 50, 40, 30, or 20 amino acid residues.

The present invention also relates to therapeutic and diagnostic methods and compositions containing the targeting retro-inverted peptides.

The invention provides compositions comprising the targeting retro-inversion peptides of the invention bound to a material comprising an active agent. Such compositions have use in targeting the active agent to the GIT and/or in facilitating transfer through the lumen of the GIT into the systemic circulation in a human or animal subject. The retro-inverted D-peptides also have general utility in targeting active agents to selected sites/selected tissues in a human or animal subject in which the receptors or other related receptors are expressed. For instance, where the retro-inverted D-peptides bind to other receptors, such as related receptors, splice variants of the receptors or related receptors which exist as a superfamily, or where the peptides bind through non-specific interactions, such as non-specific ion-pairings, hydrogen bonding or hydrophobic pairings, they can be used to deliver drugs to tissues or cell types in mammals or humans that express these receptors. Additionally, when the active agent is an imaging agent, such compositions can be administered in vivo to image selected sites/selected tissues, such as the GIT (or particular transport receptors thereof). Other active agents include but are not limited to: any drug or antigen or any drug- or antigen-loaded or drug- or antigen-encapsulated nanoparticle, microparticle, liposome, or micellar formulation capable of eliciting a biological response in a human or animal. Examples of drug- or antigen-loaded or drug- or antigen-encapsulated formulations include those in which the active agent is encapsulated or loaded into nano- or microparticles, such as biodegradable nano- or microparticles, and which have the targeting retro-inversion peptide adsorbed, coated or covalently bound, such as directly linked or linked via a linking moiety, onto the surface of the nano- or microparticle. Additionally, the targeting retro-inverted peptide can form the nano- or microparticle itself or the targeting retro-inverted peptide can be covalently attached to the polymer or polymers used in the production of the biodegradable nano- or microparticles or drug-loaded or drug-encapsulated nano- or microparticles or the peptide can be directly conjugated to the active agent. Such conjugation to active agents include proteins in which the retro-inverted peptide is conjugated directly to the protein or peptide active agent of interest. Additionally, the retro-inverted peptides of this invention can be attached to the building blocks or subunits or polymer monomers used in the synthesis of the base polymers.

In a preferred embodiment, the invention provides for treatment of various diseases and disorders by administration of a therapeutic compound (termed herein "Therapeutic"). Such "Therapeutics" include but are not limited to: targeting retro-inversion peptide bound to an active agent of value in the treatment or prevention of a disease or disorder (preferably a mammalian, most preferably human, disease or disorder). The active agent is preferably a drug.

Any drug known in the art may be used, depending upon the disease or disorder to be treated or prevented, and the type of subject to which it is to be administered. As used herein, the term "drug" includes, without limitation, any pharmaceutically active agent. Representative drugs include, but are not limited to, peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins, and antidiuretic agents. Typical drugs include peptides, proteins or hormones such as insulin, calcitonin, calcitonin gene regulating protein, atrial natriuretic protein, colony stimulating factor, betaseron, erythropoietin (EPO), interferons such as α, β or γ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogs thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogs thereof; anti-migraine agents such as heparin, hirudin, and analogs thereof; anti-coagulant agents such as scopolamine, ondansetron, domperidone, etoclopramide, and analogs thereof; cardiovascular agents, anti-hypertensive agents and vasodilators such as diltiazem, clonidine, nifedipine, verapamil, isosorbide-5-mononitrate, organic nitrates, agents used in treatment of heart disorders and analogs thereof; sedatives such as benzodiazeines, phenothiozines and analogs thereof; narcotic antagonists such as naltrexone, naloxone and analogs thereof; chelating agents such as deferoxamine and analogs thereof; anti-diuretic agents such as desmopressin, vasopressin and analogs thereof; anti-anginal agents such as nitroglycerine and analogs thereof; anti-neoplastics such as 5-fluorouracil, bleomycin and analogs thereof; prostaglandins and analogs thereof; and chemotherapy agents such as vincristine and analogs thereof. Representative drugs also include but are not limited to antisense oligonucleotides, genes, gene correcting hybrid oligonucleotides, ribozymes, aptameric oligonucleotides, triple-helix forming oligonucleotides, inhibitors of signal transduction pathways, tyrosine kinase inhibitors and DNA modifying agents. Drugs that can be used also include, without limitation, systems containing gene therapeutics, including non-viral systems for therapeutic gene delivery and viral vector systems for therapeutic genes which are modified with a retro-inversion peptide post virus purification.

In a preferred embodiment, a Therapeutic is therapeutically or prophylactically administered to a human patient.

Additional descriptions and sources of Therapeutics that can be used according to the invention are found in various Sections herein.

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably a human.

As will be clear, any disease or disorder of interest amenable to therapy or prophylaxis by providing a drug in vivo systemically or by targeting a drug (by linkage to a targeting retro-inversion peptide of the present invention) in vivo to the GIT or other selected sites, selected tissues or cell types which contain the receptor or other receptors, such as related receptors, splice variants of the receptors, related receptors which exist as a superfamily or to which the retro-inverted peptide interacts through non-specific interaction, such as non-specific ion-pairings or hydrogen bondings or hydrophobic pairings (using any route of administration) can be treated or prevented by administration of a Therapeutic of the invention. Such diseases may include but are not limited to hypertension, diabetes, osteoporosis, hemophilia, anemia, cancer, migraine, and angina pectoris, to name but a few.

Any route of administration known in the art may be used, including but not limited to oral, nasal, topical, intravenous, intraperitoneal, intradermal, mucosal, intrathecal, intramuscular, etc. Preferably, administration is oral; in such an embodiment the targeting retro-inverted peptide according to this invention acts advantageously to facilitate transport of the therapeutic active agent through the lumen of the GIT into the portal, hepatic or systemic circulation.

The present invention also provides therapeutic compositions or formulations. In a specific embodiment of the invention, a targeting retro-inversion peptide is associated with a therapeutically or prophylactically active agent, preferably a drug or drug-containing nano- or microparticle. More preferably, the active agent is a drug encapsulating or drug loaded nano- or microparticle, such as a biodegradable nano- or microparticle, in which the peptide is physically adsorbed or coated or covalently bonded, such as directly linked or linked via a linking moiety, onto the surface of the nano- or microparticle. Alternatively, the peptide can form the nano- or microparticle itself or can be directly conjugated to the active agent. Preferably the particles range in size from 10 nm and 500 μm, more preferably 50 to 800 nm, most preferably 200-600 nm.

Thus, in a specific embodiment, a targeting retro-inversion peptide is bound to a slow-release (controlled release) device containing a drug. In a specific embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)).

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, sorbitol, trehelose and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient.

The active agent of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

According to this invention, a targeting retro-inverted peptide may also be used as an immunogen to generate antibodies which immunospecifically bind such an immunogen. Such antibodies include but are not limited to polyclonal, monoclonal, chimeric, single chain, Fab fragments, and a Fab expression library.

These antibodies can be used in methods relating to the localization and activity of the targeting retro-inversion peptide sequences of the invention, e.g., for imaging these peptides after in vivo administration (e.g., to monitor treatment efficacy), measuring levels thereof in appropriate physiological samples, in diagnostic methods, etc. For instance, antibodies or antibody fragments specific to a domain of a targeting retro-inversion peptide, such as a dansyl group or some other epitope introduced into the peptide, can be used to 1) identify the presence of the peptide on a nanoparticle or other substrate; 2) quantify the amount of peptide on the nanoparticle; 3) measure the level of the peptide in appropriate physiological samples; 4) perform immunohistology on tissue samples; 5) image the peptide after in vivo administration; 6) purify the peptide from a mixture using an immunoaffinity column, 7) bind or fix the peptide to the surface of nanoparticle or 8) when a tag is also added to either an active-agent containing particle or the active agent itself, track the fate of both the particle/active agent and the targeting retro-inversion peptide so as to determine if and/or where they become separated. Use 7 above envisions attaching the antibody (or fragment of the antibody) to the surface of drug-loaded nanoparticles or other substrates and then incubating this conjugate with the peptide. This procedure results in binding of the peptide in a certain fixed orientation, resulting in a particle that contains the peptide bound to the antibody in such a way that the peptide is fully active. Additionally, antibodies or antibody fragments specific to a domain of a targeting retro-inverted peptide 9) can be used in confocal microscopy imaging techniques or other imaging techniques in order to demonstrate or confirm or identify the location or localization of the peptide on the surface of a nano- or microparticle, 10) can be used in confocal microscopy imaging techniques or other imaging techniques in order to demonstrate or confirm or identify the location or localization of the peptide on the surface of a nanoparticle or microparticle which has also been loaded with a fluorescent agent, 11) in the case of nanoparticles or microparticles coated with the peptide which have been sliced into two halves by a microtone or other suitable techniques, the antibody can be used in suitable quantitative techniques such as confocal microscopy imaging techniques or other quantitative imaging techniques in order to identify or quantitate the relative distribution of the peptide between the surface of the nanoparticle or microparticle and the subsurface interior matrix of the nanoparticles or microparticles, 12) can be used in confocal microscopy imaging techniques or other imaging techniques in order to demonstrate or confirm or identify the location of a peptide on the surface of a nanoparticle or microparticle which has been loaded with a fluorescent agent such as TRME or fluorascene, 13) can be used to identify which epitope or domain of the peptide is responsible for identification by the antibody; peptide derivatives such as cyclic forms or derivatives containing intra-chain disulphide bonds or other intra-chain bonds can also be used in mapping studies in order to identify which domain or epitope of the peptide is responsible for recognition by the antibody; 14) in the case of peptide derivatives in which the epitope or domain responsible for binding to a target receptor is flanked by di-sulphide bond or other intra-chain bonds and in which this domain is also responsible for binding to the antibody, the antibody can be used to determine if that epitope or domain is exposed or available for binding to the antibody when the peptide or derivative is coated onto the surface of a nanoparticle, microparticle or other substance, 15) can be used where the epitope or domain on the peptide which binds to the target receptors in the human gastro-intestinal tract or the target receptors on model epithelial cells such as Caco-2 cells or polarised Caco-2 cells and where this epitope or domain on the peptide is also responsible for binding by the antibody, the antibody can be used in competition studies to compete for the binding of the peptide to its target receptor sites and 16) where the epitope or domain on the peptide which binds to the target receptors in the human gastro-intestinal or the target receptors on model epithelial cells such as Caco-2 cells or polarised Caco-2 cells and where this epitope or domain on the peptide is also responsible for binding by the antibody, the antibody can be used in competition studies in which nanoparticles or microparticles are coated with the peptide and are used in cell binding studies and/or in receptor binding studies.

Abtides (or Antigen binding peptides) specific to a domain of targeting retro-inverted peptide, such as a dansyl group or some other epitope introduced into the peptide, can be used for the same purposes identified above for antibodies.

The retro-inverted peptides of this invention may be prepared by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394-1397; Marki et al., 1981, J. Am. Chem. Soc. 103:3178 and in U.S. Pat. Nos. 4,305,872 and 4,316,891. In a preferred aspect, an automated peptide synthesizer is employed.

By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3,-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenyl-ethoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the Fastmoc protocol. The following side chain protected Fmoc amino acid derivatives are used: FmocArg(Pmc)OH; FmocAsn(Mbh)OH; FmocAsp($^t$Bu)OH; FmocCys(Acm)OH; FmocGlu($^t$Bu)OH; FmocGln(Mbh)OH; FmocHis(Tr)OH; FmocLys(Boc)OH; FmocSer($^t$Bu)OH; FmocThr($^t$Bu)OH; FmocTyr($^t$Bu)OH. [Abbreviations: Acm, acetamidomethyl; Boc, tert-butoxycarbonyl; $^t$Bu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using approximately 20% piperidine in NMP. At the end of each synthesis the amount of peptide present is assayed by ultraviolet spectroscopy. A sample of dry peptide resin (about 3-10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Peptide substitution (in mmol g$^{-1}$) can be calculated according to the equation:

$$\text{substitution} = \frac{A \times v}{7800 \times w} \times 1000$$

where A is the absorbance at 301 nm, v is the volume of 20% piperidine in DMA (in ml), 7800 is the extinction coefficient (in mol$^{-1}$dm$^3$cm$^{-1}$) of the dibenzofulvene-piperidine adduct, and w is the weight of the peptide-resin sample (in mg).

Finally, the N-terminal Fmoc group is cleaved using 20% piperidine in DMA, then acetylated using acetic anhydride and pyridine in DMA. The peptide resin is thoroughly washed with DMA, CH$_2$Cl$_2$ and finally diethyl ether.

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoroacetic acid (TFA). A total volume of approximately 50 ml of these reagents are used per gram of peptide-resin. The following ratio is used: TFA:EtSMe:EDT:PhSme (10:0.5:0.5:0.5). The mixture is stirred for 3 h at room temperature under an atmosphere of N$_2$. The mixture is filtered and the resin washed with TFA (2×3 ml). The combined filtrate is evaporated in vacuo, and anhydrous diethyl ether added to the yellow/orange residue. The resulting white precipitate is isolated by filtration. See King et al., 1990, Int. J. Peptide Protein Res. 36:255-266 regarding various cleavage methods.

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

The peptides of the present invention may be linked to other molecules (e.g., a detectable label, a molecule facilitating adsorption to a solid substratum, or a toxin, according to various embodiments of the invention) by methods that are well known in the art. Such methods include the use of homobifunctional and heterobifunctional cross-linking molecules.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., 1984, Science 223:1304-1306.

Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. Some examples of heterobifunctional reagents containing reactive disulfide bonds include N-succinimidyl 3-(2-pyridyl-dithio)propionate (Carlsson et al., 1978, Biochem J. 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce.

Additional information regarding how to make and use these as well as other polyfunctional reagents may be obtained from the following publications or others available in the art: Carlsson et al., 1978, Biochem. J. 173:723-737; Cumber et al., 1985, Methods in Enzymology 112:207-224; Jue et al., 1978, Biochem 17:5399-5405; Sun et al., 1974, Biochem. 13:2334-2340; Blattler et al., 1985, Biochem. 24:1517-152; Liu et al., 1979, Biochem. 18:690-697; Youle and Neville, 1980, Proc. Natl. Acad. Sci. USA 77:5483-5486; Lerner et al., 1981, Proc. Natl. Acad. Sci. USA 78:3403-3407; Jung and Moroi, 1983, Biochem. Biophys. Acta 761:162; Caulfield et al., 1984, Biochem. 81:7772-7776; Staros, 1982, Biochem. 21:3950-3955; Yoshitake et al., 1979, Eur. J. Biochem. 101:395-399; Yoshitake et al., 1982, J. Biochem. 92:1413-1424; Pilch and Czech, 1979, J. Biol. Chem. 254: 3375-3381; Novick et al., 1987, J. Biol. Chem. 262:8483-8487; Lomant and Fairbanks, 1976, J. Mol. Biol. 104:243-261; Hamada and Tsuruo, 1987, Anal. Biochem. 160:483-488; Hashida et al., 1984, J. Applied Biochem. 6:56-63.

Additionally, methods of cross-linking are reviewed by Means and Feeney, 1990, Bioconjugate Chem. 1:2-12.

Synthesis and Characterization of Targeting Retro-Inverted Peptides

Similar to that described in the above-referenced WO 98/51325, synthetic dansylated peptides were manufactured at Genosys Biotechnologies, UK and Anaspec Inc., USA. Characterisation profiles included appearance, solubility, HPLC and mass spectrometry (minimum purity >95%). Table 1 shows the primary sequences for both the retro-inverted peptide synthesized by reference to particular GIT targeting agents and the original GIT targeting agents themselves.

| SEQ ID NO: | Name | Description | Sequence |
|---|---|---|---|
| 1 | SEQ ID NO:1 | PAX2 15 mer fragment-D form retroinversion | rtrlrrnhsshkant |
| 2 | SEQ ID NO:2 | P31 16 mer fragment-D form retroinversion | gphrrgrpnsrsskrt |

-continued

| SEQ ID NO: | Name | Description | Sequence |
|---|---|---|---|
| 3 | SEQ ID NO:3 | HAX42 14 mer fragment-D form retroinversion | gtsngngccnydgp |
| 4 | SEQ ID NO:4 | PAX2 15 mer fragment | TNAKHSSHNRRLRTR |
| 5 | SEQ ID NO:5 | P31 16 mer fragment | TRKSSRSNPRGRRHPG |
| 6 | SEQ ID NO:6 | HAX42 14 mer fragment | PGDYNCCGNGNSTG |
| 9 | ZElan144 | dansylated PAX2 15 mer fragment-D form retroinversion | K(dns)-rtrlrrnhsshkant |
| 10 | ZElan145 | dansylated P31 16 mer fragment-D form retroinversion | K(dns)-gphrrgrpnsrsskrt |
| 11 | ZElan146 | dansylated HAX42 14 mer fragment-D form retroinversion | K(dns)-gtsngngccnydgp |
| 12 | ZElan129 | dansylated PAX2 15 mer fragment | K(dns)-TNAKHSSHNRRLRTR |
| 13 | ZElan031 | dansylated P31 16 mer fragment | K(dns)-TRKSSRSNPRGRRHPG |
| 14 | ZElan091 | dansylated HAX42 14 mer fragment | K(dns)-PGDYNCCGNGNSTG |

Analysis of Binding of Dansylated Peptides to Caco-2 Cell Membrane Fractions by ELISA Similar to the methods described in the above-referenced WO 98/51325, Caco-2 cell membrane (P100) and cytosolic (S100) fractions were prepared using a modification of the method described in Kinsella, B. T., O'Mahony, D. J. and G. A. FitzGerald, 1994, J. Biol. Chem. 269(47): 29914-29919. Confluent Caco-2 cell monolayers (grown in 75 cm² flasks for up to 1 week at 37° C. and 5% $CO_2$) were washed twice in Dulbecco's PBS (DPBS) and the cells were harvested by centrifugation at 1000 rpm after treatment with 10 mM EDTA-DPBS. The cells were washed 3 times in DPBS and the final cell pellet was resuspended in 3 volumes of ice cold HED buffer (20 mM HEPES (pH 7.67), 1 mM EGTA, 0.5 mM dithiothreitol, 1 mM phenylmethylsulphonyl fluoride (PMSF)). The cells were allowed to swell for 5 min on ice prior to homogenization for 30 sec. The homogenates were centrifuged at 40,000 rpm for 45 min at 4° C. The supernatant (S100) was removed and the pellet (P100) was resuspended in HEDG buffer (20 mM HEPES (pH 7.67), 1 mM EGTA, 0.5 mM dithiothreitol, 100 mM NaCl, 10% glycerol, 1 mM PMSF). Protein concentrations were determined using the Bradford assay (Bradford, M. M., 1976, Anal. Biochem. 72: 248-254).

Binding of peptides to membrane (P100) was assessed by detection of the dansyl moiety incorporated in the peptide. Costar ninety six well ELISA plates were coated with P100 fractions (100 µg/ml in 0.05 M $NaHCO_3$ (pH 9.6); 100 µl/well) overnight at 4° C. The plates were blocked with 2% Marvel-DPBS for 1 h at room temperature and washed 3 times in 1% DPBS-Tween. Peptides (200 µg/ml in 2% Marvel-DPBS) were serially diluted on the plates and incubated for 1 h at room temperature. The plates were washed 5 times and the dansylated peptides were detected using i) mouse anti-dansyl antiserum (Cytogen DB3-226.3; 1:1340 dilution in 2% Marvel-DPBS) or ii) rabbit anti-dansyl antiserum (La Jolla Diagnostics LAJD-119; 1:1000 dilutions) for 1 h at room temperature. The plates were washed 3 times prior to incubation with i) goat anti-mouse IgGλ:HRP antibody (Southern Biotechnology 1060-05; 1:10,000 dilution in 2% Marvel-DPBS) or ii) anti-rabbit IgG HRP (Sigma A-0545, 1:8,000) for 1 h at room temperature. After 3 washes, reactions were visualized using K Blue Substrate and Red Stop Solution (Neogen Co. 300176 & 301475, respectively) at 650 nm.

ZElan021, full length HAX42 [K(dns)-SDHALGTNLRS-DNAKEPGDYNCCGNGNSTGRKVFNRRRPSAIPT] (SEQ ID NO:53; dansylated version is SEQ ID NO:8) was given the arbitrary value of 1.00 for binding to P100 at a given peptide concentration determined from the signal-to-noise ratio data. Table 2 shows the results of P100 assays with the HAX42 related peptides ZElan021, Zelan091 and ZElan146. Assay number 1 was at 20 µg/ml; 2 and 3 were at 50 µg/ml; and 4 through 8 were at 25 µg/ml. The results for the retro-inverted form, Zelan 146 show reasonable binding compared to the HAX42 fragment Zelan091 and that the activity of the GIT targeting agent was not eliminated when converted to its retro-inverted form.

TABLE 2

| Peptide | P100 assay number | | | | | | | |
|---|---|---|---|---|---|---|---|---|
| | 1 | 2 | 3 | 4 | 5 | 6 | 7 | 8 |
| ZElan021 | 1.00 | 1.00 | 1.00 | 1.00 | 1.00 | 1.00 | 1.14 | 0.94 |
| ZElan091 | | | | 2.02 | 1.37 | 1.20 | 0.85 | |
| ZElan146 | | | | | | | 0.36 | 0.72 |

$K_D$ values, or the concentration of the peptide required to reach half maximal binding to Caco-2 P100 fractions, are given in Table 3 for ZElan021, full length HAX42, [K(dns)-SDHALGTNLRSDNAKEPGDYNCCGNGN-STGRKVFNRRRPSAIPT] (SEQ ID NO:53; dansylated version is SEQ ID NO:8), HAX42 fragment ZElan091, and the retro-inverted form of this fragment, ZElan146 as well as for ZElan018, full length PAX2, [K(dns)-STPPSREAYSRPYS-VDS DSDTNAKHSSHNRRLRTRSRPNG] (SEQ ID NO:7; dansylated version is SEQ ID NO:15), PAX2 fragment ZElan129, and the retro-inverted form of this fragment, ZELan144.

| Name | Sequence | $K_D$ (µmol) |
|---|---|---|
| ZElan018 | K(dns)-STPPSREAYSRPYSVDSDSDTNAKHSSH NRRLRTRSRPNG (SEQ ID NO:7) | >50.0 |
| ZElan129 | K(dns)-TNAKHSSHNRRLRTR (SEQ ID NO:12) | 29.6 |
| ZElan144 | K(dns)-rtrlrrnhsshkant (SEQ ID NO:9) | 28.8 |
| ZElan021 | K(dns)-SDHALGTNLRSDNAKEPGDYNCCGNG NSTGRKVFNRRRPSAIPT (SEQ ID NO:8) | 6.7 |
| ZElan091 | K(dns)-PGDYNCCGNGNSTG (SEQ ID NO:14) | 0.75 |
| ZElan146 | K(dns)-gtsngngccnydgp (SEQ ID NO:11) | 21.65 |

Manufacture and Analysis of Peptide-Coated Insulin Loaded PLGA Particles

Insulin-loaded PLGA particles are coated with retro-inverted peptides according to this invention or GIT targeting agents by the coacervation processes described in the above-referenced WO 98/51325. In particular, solid particles containing an active agent are formed from a polymer and have a particle size of between about 10 nm and 500 µm, most preferably 50 to 800 nm. In addition the particles contain targeting retro-inverted peptides which are incorporated into the particles using a number of methods as outlined below and described in the above-referenced WO 98/51325.

The organic phase (B) polymer of the general method given below may be soluble, permeable, impermeable, biodegradable or gastroretentive. The polymer may consist of a mixture of polymer or copolymers and may be a natural or synthetic polymer. Representative biodegradable polymers include without limitation polyglycolides; polylactides; poly(lactide-co-glycolides), including DL, L and D forms; copolyoxalates; polycaprolactone; polyesteramides; polyorthoesters; polyanhydrides; polyalkylcyanoacrylates; polyhydroxybutyrates; polyurethanes; albumin; casein; citosan derivatives; gelatin; acacia; celluloses; polysaccharides; alginic acid; polypeptides; and the like, copolymers thereof, mixtures thereof and stereoisomers thereof. Representative synthetic polymers include alkyl celluloses; hydroxalkyl celluloses; cellulose ethers; cellulose esters; nitrocelluloses; polymers of acrylic and methacrylic acids and esters thereof; dextrans; polyamides; polycarbonates; polyalkylenes; polyalkylene glycols; polyalkylene oxides; polyalkylene terephthalates; polyvinyl alcohols; polyvinyl ethers; polyvinyl esters; polyvinyl halides; poyvinylpyrrolidone; polysiloxanes and polyurethanes and co-polymers thereof.

Typically, particles are formed using the following general method:

An aqueous solution (A) of a polymer, surface active agent, surface stabilising or modifying agent or salt, or surfactant preferably a polyvinyl alcohol (PVA) or derivative with a % hydrolysis 50-100% and a molecular weight range 500-500,000, most preferably 80-100% hydrolysis and 10,000-150,000 molecular weight, is introduced into a vessel. The mixture (A) is stirred under low shear conditions at 10-2000 rpm, preferably 100-600 rpm. The pH and/or ionic strength of this solution may be modified using salts, buffers or other modifying agents. The viscosity of this solution may be modified using polymers, salts, or other viscosity enhancing or modifying agents.

A polymer, preferably poly(lacide-co-glycolide), polylactide, polyglycolide or a combination thereof or in any enantiomeric form or a covalent conjugate of the these polymers with a targeting ligand is dissolved in water miscible organic solvents to form organic phase (B). Most preferably, a combination of acetone and ethanol is used in a range of ratios from 0:100 acetone:ethanol to 100:0 acetone:ethanol depending upon the polymer used.

Additional polymer(s), peptide(s) sugars, salts, natural/biological polymers or other agents may also be added to the organic phase (B) to modify the physical and chemical properties of the resultant particle product.

A drug or bioactive substance may be introduced into either the aqueous phase (A) or the organic phase (B). A targeting retro-inversion peptide or GIT targeting agent may also be introduced into either the aqueous phase (A) or the organic phase (B) at this point.

The organic phase (B) is added into the stirred aqueous phase (A) at a continuous rate. The solvent is evaporated, preferably by a rise in temperature over ambient and/or the use of a vacuum pump. The particles are now present as a suspension (C). A targeting retro-inversion peptide or GIT targeting agent may be introduced into the stirred suspension at this point.

A secondary layer of polymer(s), peptide(s) sugars, salts, natural/biological polymers or other agents may be deposited on to the pre-formed particulate core by any suitable method at this stage.

The particles (D) are then separated from the suspension (C) using standard colloidal separation techniques, preferably by centrifugation at high 'g' force, filtration, cross-flow filtration, gel permeation chromatography, affinity chromatography or charge separation techniques. The supernatant is discarded and the particles (D) re-suspended in a washing solution (E) preferably water, salt solution, buffer or organic solvent(s). The particles (D) are separated from the washing liquid in a similar manner as previously described and re-washed, commonly twice. A targeting ligand may be dissolved in washing solution (E) at the initial, intermediate and/or at the final washing stage and may be used to wash the particles (D).

The particles may then be dried. Particles may then be further processed for example, tabletted, encapsulated or spray dried.

The release profile of the particles formed above may be varied from immediate to controlled or delayed release dependent upon the formulation used and/or desired.

Drug loading may be in the range 0-90% w/w. Targeting retro-inversion peptide or GIT targeting agent loading may be in the range 0-90% w/w.

Insulin-loaded PLGA (RG504H) nanoparticles were manufactured as given above for the following targeting ligands: full length HAX42 (ZElan021), full length PAX2 (ZElan018), HAX42 fragment ZElan091, PAX2 fragment ZElan129, HAX42 fragment retro-inverted peptide ZElan146 and PAX2 fragment retro-inverted peptide ZElan144. Bovine insulin potency (HPLC) and peptide loading (dansyl fluorescence) were assessed prior to analysis of insulin delivery in Wistar rats using the open loop model. Table 4 shows the insulin potency and targeting peptide loading of the PLGA particles.

TABLE 4

| Peptide | Insulin Potency (mg/g) | Peptide Loading (µg/mg) |
|---------|------------------------|-------------------------|
| ZELAN 018 | 47.0 | 1.68 |
| ZELAN 129 | 59.0 | 0.85 |
| ZELAN 144 | 58.2 | 0.68 |
| ZELAN 021 | 49.7 | 2.63 |
| ZELAN 091 | 57.1 | 1.87 |
| ZELAN 146 | 53.8 | 1.77 |

Animal Studies

In vivo assessment of oral insulin bioavailability of various targeting retro-inversion peptides was undertaken using open-loop studies study in which the test solution containing nanoparticles described above (Table 4) was injected directly into the ileum in Wistar rats similar to the protocols described in the above-referenced WO 98/51325. In short, Wistar rats (300-350 g) were fasted for 4 hours and anaesthetized by intramuscular administration 15 to 20 minutes prior to administration of the test solution with a solution of ketamine [0.525 ml of ketamine (100 mg/ml) and 0.875 ml of acepromazine maleate-BP ACP (2 mg/ml)]. The rats were then injected with a test solution (injection volume: 1.5 ml PBS) intra-duodenally at 2-3 cm below the pyloris. Insulin (fast-acting bovine; 28.1 iu/mg) was incorporated in the particles as described above for a total of 300 iu insulin (approximately 210 mg particles). Blood glucose values for the rats were measured using a Glucometer™ (Bayer; 0.1 to 33.3 m/mol/L); plasma insulin values were measured using a Phadeseph RIA Kit™ (Upjohn Pharmacia; 3 to 240 μU/ml-assayed in duplicate). Systemic and portal blood was sampled.

Study groups included animals receiving test solutions containing particles coated with the following peptides shown in Table 4. Control groups included: 1) PBS control (1.5 ml) Open-Loop; 2) Insulin solution (1 iu/0.2 ml) subcutaneous; 3) Insulin particles, no peptide.

Figure 2:
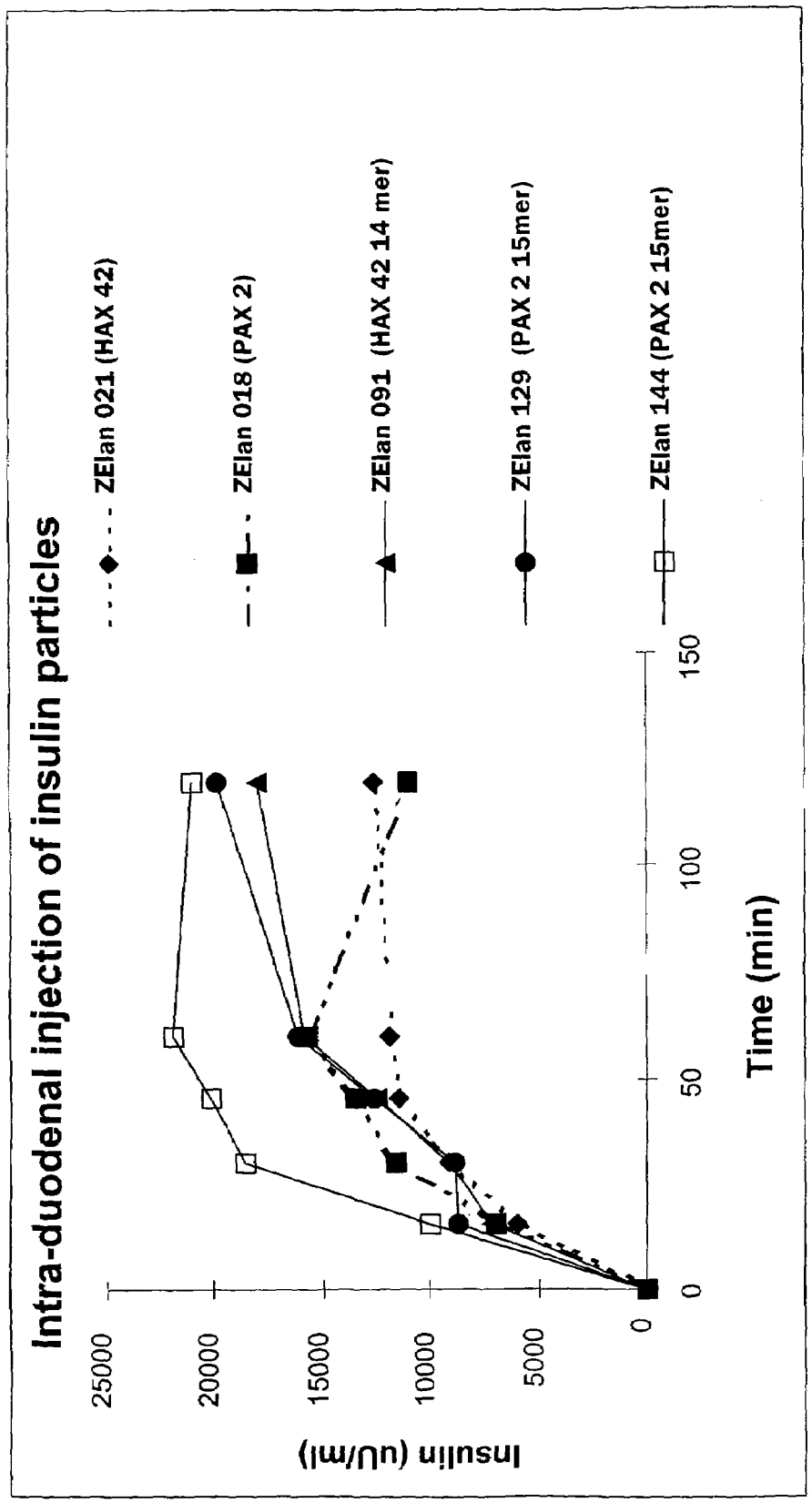
FIG. 2 shows the systemic insulin levels following intestinal administration of control ZElan 021 coated insulin-containing particles, ZElan 018 coated insulin-containing particles, ZElan091 coated insulin-containing particles, ZElan129 coated insulin-containing particles and ZElan144 coated insulin-containing particles according to this invention (300 iu insulin loading).

Table 5 shows the insulin bioavailability for the insulin-loaded nanoparticles described above (surface modified with targeting retro-inversion peptide or GIT targeting agent) expressed as a % bioavailability of the administered oral dose compared to the reference insulin sub-cutaneous dose. FIGS. 1 and 2 show the (1) systemic blood glucose and (2) insulin levels following intestinal administration of control (PBS); ZElan 021 coated insulin-containing particles, ZElan 018 coated insulin-containing particles, ZElan091 coated insulin-containing particles, ZElan129 coated insulin-containing particles and ZElan 144 coated insulin-containing particles according to this invention (300 iu insulin loading).

TABLE 5

| Targeting Ligand | % Insulin Bio-availability |
|---|---|
| HAX42 ZELAN 021 | 12.6 |
| PAX2 ZELAN 018 | 13.04 |
| HAX42 14 MER ZELAN 091 | 11.4 |
| HAX42 14 MER ZELAN 146 (retro-inversion) | 2.1 |
| PAX2 15 MER ZELAN 144 (retro-inversion) | 10.8 |
| PAX2 15 MER ZELAN 129 | 14.3 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A d-form retro-inverted peptide comprising an amino acid sequence selected from the group consisting of SEQ ID NO:1 (ZElan144), SEQ ID NO:2 (ZElan145), and SEQ ID NO:3 (ZElan146) wherein said peptide binds to a domain of a gastro-intestinal tract transport receptor selected from the group consisting of amino acids 29-273 of human intestinal oligopeptide transporter (HPT1), amino acids 391-571 of human oligopeptide transporter (hPEPT1), amino acids 387-685 of human D2 clone (D2H), and amino acids 272-667 of human sucrase isomaltose (hSI), wherein said peptide is no more than 50 amino acid residues.

2. The peptide of claim 1, wherein the peptide is no more than 40 amino acid residues.

3. The peptide of claim 1, wherein the peptide is no more than 30 amino acid residues.

4. The peptide of claim 1, wherein the peptide is no more than 20 amino acid residues.

5. A pharmaceutical composition comprising a therapeutically effective amount of a composition comprising the peptide of claim 1 and a pharmaceutically acceptable carrier.

6. A composition comprising the peptide of claim 1, wherein the peptide is coated onto the surface of a nanoparticle or microparticle, absorbed onto the surface of a nanoparticle or microparticle, or covalently bonded to the surface of a nanoparticle or microparticle.

7. A nanoparticle or microparticle formed from the peptide of claim 1.

* * * * *

UNITED STATES PATENT AND TRADEMARK OFFICE
CERTIFICATE OF CORRECTION

| | | |
|---|---|---|
| PATENT NO. | : 7,491,796 B1 | Page 1 of 1 |
| APPLICATION NO. | : 09/443986 | |
| DATED | : February 17, 2009 | |
| INVENTOR(S) | : O'Mahony | |

It is certified that error appears in the above-identified patent and that said Letters Patent is hereby corrected as shown below:

On the Title Page, Item 54 and Column 1, Lines 1-3:
 Please correct the title to read as: RETRO-INVERSION PEPTIDES THAT TARGET GIT TRANSPORT RECEPTORS AND RELATED METHODS On the Title Page, Item 74:
 Please correct the Attorney, Agent, or Firm to read as: Myers Bigel Sibley & Sajovec, P.A.

Signed and Sealed this

Twenty-first Day of April, 2009

JOHN DOLL
*Acting Director of the United States Patent and Trademark Office*